Figure 1A:
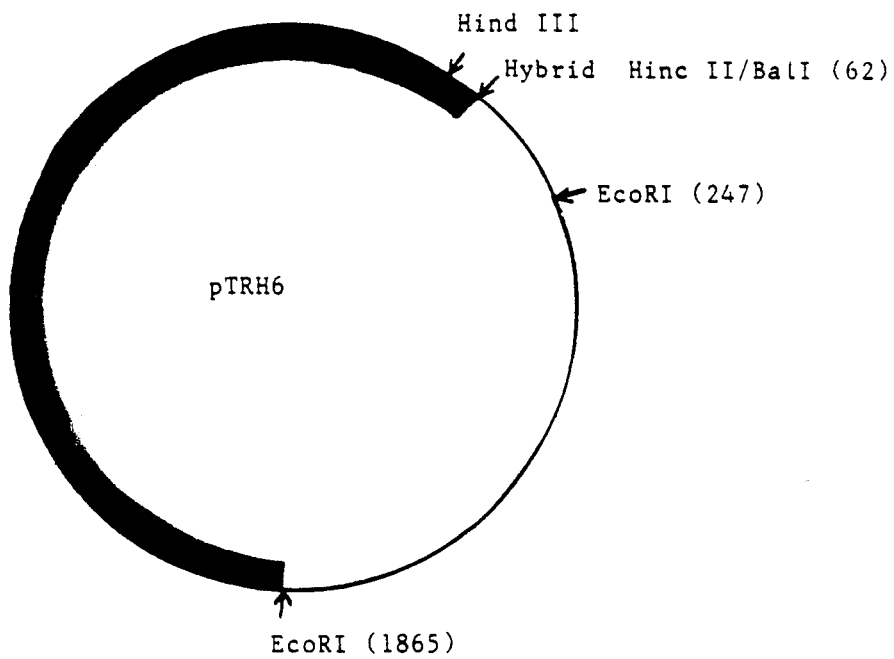

United States Patent [19]

Browne et al.

[11] Patent Number: 5,302,390

[45] Date of Patent: Apr. 12, 1994

[54] HYBRID PROTEINS OF HUMAN PLASMINOGEN AND HUMAN T-PA, PHARMACEUTICAL COMPOSITIONS AND METHODS OF TREATMENT

[75] Inventors: Michael J. Browne; Jeffery H. Robinson; Richard A. G. Smith, all of Epsom; Sarkis B. Kalindjian, Banstead, all of England

[73] Assignee: Beecham Group plc, United Kingdom

[21] Appl. No.: 953,312

[22] Filed: Sep. 29, 1992

Related U.S. Application Data

[63] Continuation of Ser. No. 808,979, Dec. 17, 1991, abandoned, which is a continuation of Ser. No. 212,910, Jun. 29, 1988, abandoned.

[30] Foreign Application Priority Data

| Jul. 1, 1987 [GB] | United Kingdom | 8715391 |
| Jul. 1, 1987 [GB] | United Kingdom | 8715392 |
| Aug. 14, 1987 [GB] | United Kingdom | 8719279 |

[51] Int. Cl.$^5$ .......... C12N 9/64; C12N 15/00; C12N 9/68; A61K 37/547

[52] U.S. Cl. .......... 424/94.64; 424/94.63; 435/212; 435/219; 435/226; 435/217

[58] Field of Search .......... 435/212, 219, 217, 226; 424/94.63, 94.64

[56] References Cited

U.S. PATENT DOCUMENTS

| 4,752,581 | 0/1988 | Robinson | 435/217 |
| 4,908,204 | 0/1990 | Robinson | 424/94.2 |
| 5,073,494 | 12/1991 | Heyneker et al. | 435/226 |

FOREIGN PATENT DOCUMENTS

| 9879 | 8/1980 | European Pat. Off. | A61K 37/48 |
| 091240 | 10/1983 | European Pat. Off. | C12N 9/96 |
| 151308 | 8/1985 | European Pat. Off. | C12N 9/96 |
| 152736 | 8/1985 | European Pat. Off. | A61K 37/54 |
| 155387 | 9/1985 | European Pat. Off. | A61K 37/54 |
| 199574 | 10/1986 | European Pat. Off. | . |
| 201153 | 11/1986 | European Pat. Off. | . |
| 213794 | 3/1987 | European Pat. Off. | C12N 15/00 |
| 225286 | 6/1987 | European Pat. Off. | . |
| 227462 | 7/1987 | European Pat. Off. | . |
| 233013 | 8/1987 | European Pat. Off. | . |
| 250071 | 12/1987 | European Pat. Off. | C12N 9/48 |
| 273774 | 7/1988 | European Pat. Off. | . |
| 293934 | 12/1988 | European Pat. Off. | C12N 9/50 |
| 3537176 | 7/1986 | Fed. Rep. of Germany | . |
| WO8601538 | 3/1986 | PCT Int'l Appl. | . |
| WO8704722 | 8/1987 | PCT Int'l Appl. | . |
| 8705934 | 10/1987 | PCT Int'l Appl. | C12N 15/00 |

OTHER PUBLICATIONS

Forsgren, M. et al., *FEBS Letters*, 213:254, 1987.
Castellino, F. J., *Chemical Reviews*, 81:431, 1981.
Tate, Keri M. et al., *Biochemistry*, 26:338, 1987.
Robbins et al, Biochemistry (1986), 25, 3603–3611.
Robbins et al., Biochemistry (1987), 26, 4661–4667.
Sturzbecher, Biomed Biochim. Acta, 45 (1986), pp. 1405–1410.
Sturzebecher et al, Thrombosis Research, 47 (1987), pp. 699–703.
Kalindjian et al, Biological Abstracts, 85 (1988) 60983.

*Primary Examiner*—Robert J. Hill, Jr.
*Assistant Examiner*—Marianne Porta Allen
*Attorney, Agent, or Firm*—Rosenman & Colin

[57] ABSTRACT

A hybrid plasminogen activator which comprises the five kringle domains of plasminogen linked to the B-chain of t-PA or u-PA via an amino acid sequence comprising, respectively, the t-PA cleavage site between residues 275 and 276 and the cysteine residue 264 of t-PA or the u-PA cleavage site between residues 158 and 159 and the cysteine residue 148 of u-PA, or a derivative of a plasminogen activator comprising the serine protease domain of t-PA or u-PA, in which the catalytic site essential for plasminogen activator activity is blocked by a 2-aminobenzoyl group substituted in the 3- or 4-position with a halogen atom and optionally further substituted with one or more weakly electron-withdrawing or electon-donating groups, wherein the pseudo first order rate constant for hydrolysis of the derivative is in the range $6.0 \times 10^{-5}$ to $4.0 \times 10^{-4} \text{sec}^{-1}$ when measured in a buffer system consisting of 0.05M sodium phosphate, 0.1M sodium chloride, 0.01% v/v detergent comprising polyoxyethylenesorbitan monoleate having a molecular weight of approximately 1300, at pH 7.4 at 37° C.

14 Claims, 21 Drawing Sheets pTRH01 pTRH02 pTRH25

Plasmid PSV₂dhfr

Plasmid BPV-MT-XhoI

Plasmid pTRH69

Plasmid pTRH71

Plasmid pTHRH11

FIG. 16A

```
TTCTGAGCACAGGGCTGGAGAGAAACCTCTGCGAGGAGAAAGGGAAGGAGCAAGCCGTGAATTAAGGGACGCTGTGAAGCAATC
1                                                                    50

-35
        met asp ala met lys arg gly leu leu cys cys val leu leu cys
        ATG GAT GCA ATG AAG AGA GGG CTC TGC TGT GTG CTG CTG TGT
                                100
     -20                                       -10
gly ala val phe val ser pro ser gln glu ile his ala arg phe arg arg gly ala arg
GGA GCA GTC TTC GTT TCG CCC AGC CAG GAA ATC CAT GCC CGA TTC AGA AGA GGA GCC AGA
                        150
  1                                                    10
SER TYR GLN VAL ILE CYS ARG ASP GLU LYS THR GLN MET ILE TYR GLN HIS GLN
TCT TAC CAA GTG ATC TGC AGA GAT GAA AAA ACG CAG ATG ATA TAC CAG CAA CAT CAG
                200
 20                                        30
SER TRP LEU ARG PRO VAL LEU ARG SER ASN ARG VAL GLU TYR CYS TRP CYS ASN SER GLY
TCA TGG CTG CGC CCT GTG CTC AGA AGC AAC CGG GTG GAA TAT TGC TGG TGC AAC AGT GGC
    250                                                                  300
 40                                       50
ARG ALA GLN CYS HIS SER VAL PRO VAL LYS SER CYS SER GLU PRO ARG CYS PHE ASN GLY
AGG GCA CAG TGC CAC TCA GTG CCT GTC AAA AGT TGC AGC GAG CCA AGG TGT TTC AAC GGG
                                                    330
```

FIG.16B

```
 60
GLY THR CYS GLN GLN ALA LEU TYR PHE SER ASP PHE VAL CYS GLN CYS PRO GLU GLY PHE
GGC ACC TGC CAG CAG GCC CTG TAC TTC TCA GAT TTC GTG TGC CAG TGC CCC GAA GGA TTT
                                        70                      400

80                                      90
ALA GLY LYS CYS CYS GLU ILE ASP THR ARG GLY ALA THR CYS TYR GLU ASP GLN GLY ILE SER
GCT GGG AAG TGC TGT GAA ATA GAT ACC AGG GGC GCC ACG TGC TAC GAG GAC CAG GGC ATC AGC
                            450

100                                     110
TYR ARG GLY THR TRP SER THR ALA GLU SER GLY ALA GLU CYS THR ASN TRP ASN SER SER
TAC AGG GGC ACG TGG AGC ACA GCG GAG AGT GGC GCC GAG TGC ACC AAC TGG AAC AGC AGC
                500

120                                     130
ALA LEU ALA GLN LYS PRO TYR SER GLY ARG ARG PRO ASP ALA ILE ARG LEU GLY LEU GLY
GCG TTG GCC CAG AAG CCC TAC AGC GGG CGG CCA GAC GCC ATC AGG CTG GGC CTG GGG
    550                                                             600

140                                     150
ASN HIS ASN TYR CYS ARG ASN PRO ASP ARG ASP SER LYS PRO TRP CYS TYR VAL PHE LYS
AAC CAC AAC TAC TGC AGA AAC CCA GAT CGA GAC TCA AAG CCC TGG TGC TAC GTC TTT AAG
                                                            650

160                                     170
ALA GLY LYS TYR SER SER GLU PHE CYS SER THR PRO ALA CYS SER GLU GLY ASN SER ASP
GCG GGG AAG TAC AGC TCA GAG TTC TGC AGC ACC CCT GCC TGC TCT GAG GGA AAC AGT GAC
                                                700
```

FIG. 16C

```
180
CYS TYR PHE GLY ASN GLY SER ALA TYR ARG GLY THR HIS SER LEU THR GLU SER GLY ALA
TGC TAC TTT GGG AAT GGG TCA GCC TAC CGT GGC ACG CAC AGC CTC ACC GAG TCG GGT GCC
                                750                              190

200
SER CYS LEU PRO TRP ASN SER MET ILE LEU ILE GLY LYS VAL TYR THR ALA GLN ASN PRO
TCC TGC CTC CCG TGG AAT TCC ATG ATC CTG ATA GGC AAG GTT TAC ACA GCA CAG AAC CCC
                    800                     210

220
SER ALA GLN ALA LEU GLY LEU GLY LYS HIS ASN TYR CYS ARG ASN PRO ASP GLY ASP ALA
AGT GCC CAG GCA CTG GGC CTG GGC AAA CAT AAT TAC TGC CGG AAT CCT GAT GGG GAT GCC
      850                         230                                900

240
LYS PRO TRP CYS HIS VAL LEU LYS ASN ARG ARG LEU THR TRP GLU TYR CYS ASP VAL PRO
AAG CCC TGG TGC CAC GTG CTG AAG AAC CGC AGG CTG ACG TGG GAG TAC TGT GAT GTG CCC
                          250                       950

260
SER CYS SER THR CYS GLY LEU ARG GLN TYR SER GLN PRO GLN PHE ARG ILE LYS GLY GLY
TCC TGC TCC ACC TGC GGC CTG AGA CAG TAC AGC CAG CCT CAG TTT CGC ATC AAA GGA GGG
                              270       1000

280
LEU PHE ALA ASP ILE ALA SER HIS PRO TRP GLN ALA ALA ILE PHE ALA LYS HIS ARG ARG
CTC TTC GCC GAC ATC GCC TCC CAC CCC TGG CAG GCT GCC ATC TTT GCC AAG CAC AGG AGG
                                1050       290
```

FIG.16D

```
300
SER PRO GLY GLU ARG PHE LEU CYS GLY GLY ILE LEU ILE SER SER CYS TRP ILE LEU SER
TCG CCC GGA GAG CGG TTC CTG TGC GGG GGC ATA CTC ATC AGC TCC TGC TGG ATT CTC TCT
            1100

320
ALA ALA HIS CYS PHE GLN GLU ARG PHE PRO HIS HIS LEU THR VAL ILE LEU GLY ARG
GCC GCC CAC TGC TTC CAG GAG AGG TTT CCG CAC CAC CTG ACG GTG ATC TTG GGC AGA
        1150                                                    1200

340
THR TYR ARG VAL VAL PRO GLY GLU GLU GLN LYS PHE GLU VAL GLU LYS TYR ILE VAL
ACA TAC CGG GTG GTC CCT GGC GAG GAG CAG AAA TTT GAA GTC GAA AAA TAC ATT GTC
                                                         1250

360
HIS LYS GLU PHE ASP ASP THR TYR ASP ASN ASP ILE ALA LEU LEU LEU LYS SER
CAT AAG GAA TTC GAT GAT GAC ACT TAC GAC AAT GAC ATT GCG CTG CTG CAG AAA TCG
                                        1300

380
ASP SER SER ARG CYS ALA GLN GLU SER SER VAL VAL ARG THR VAL CYS LEU PRO PRO ALA
GAT TCG TCC CGC TGT GCC CAG GAG AGC AGC GTG GTC CGC ACT GTG TGC CTT CCC CCG GCG
                                    1350

400                          410
ASP LEU GLN LEU PRO ASP TRP THR GLU CYS GLU LEU SER GLY TYR GLY LYS HIS GLU ALA
GAC CTG CAG CTG CCG GAC TGG ACG GAG TGT GAG CTC TCC GGC TAC GGC AAG CAT GAG GCC
                1400
```

FIG.16E

```
420
LEU SER PRO PHE TYR SER GLU ARG LEU LYS GLU ALA HIS VAL ARG LEU TYR PRO SER SER
TTG TCT CCT TTC TAT TCG GAG CGG CTG AAG GAG GCT CAT GTC AGA CTG TAC CCA TCC AGC
        1450                                                          1500

440
ARG CYS THR SER GLN HIS LEU LEU ASN ARG VAL THR ASP ASN MET LEU CYS ALA GLY
CGC TGC ACA TCA CAA CAT TTA CTT AAC AGA GTC ACC GAC AAC ATG CTG TGT GCT GGA
                                                  1550

460
ASP THR ARG SER GLY GLY PRO GLN ALA ASN LEU HIS ASP ALA CYS GLN GLY ASP SER GLY
GAC ACT CGG AGC GGC GGG CCC CAG GCA AAC TTG CAC GAC GCC TGC CAG GGC GAT TCG GGA
                                        1600

480
GLY PRO LEU VAL CYS LEU ASN ASP GLY ARG MET THR LEU VAL GLY ILE ILE SER TRP GLY
GGC CCC CTG GTG TGT CTG AAC GAT GGC CGC ATG ACT TTG GTG GGC ATC ATC AGC TGG GGC
                                1650

500
LEU GLY CYS GLY GLN LYS ASP VAL PRO GLY VAL TYR THR LYS VAL THR ASN TYR LEU ASP
CTG GGC TGT GGA CAG AAG GAT GTC CCG GGT GTG TAC ACA AAG GTT ACC AAC TAC CTA GAC
              1700

520                         527
TRP ILE ARG ASP ASN MET ARG PRO OP
TGG ATT CGT GAC AAC ATG CGA CCG TGA
    1750
```

FIG.16F

```
CCAGGAACACCCGACTCCTCAAAAGCAAATGAGATCCCGCCTCTCTCTTCAGAAGACACTGCAAAGGCGCAGTG
                          1800
CTTCTCTACAGACTTCTCCAGACCCCACCACCGCAGAAGCGGGACTGGTCTGATTTCAGGAGAGACCCTACAGGAGAGGGAAGAGTGCAT
     1850                                                            1900
TTTCCCAGATACTTCCCATTTGGAAGTTTTCAGGACTTGGTCTGATTTCAGGATACTCTGTCAGATGGGAAGAC
                 1950                                             2030
ATGAATGCACACTAGCCTCTCCAGGAATGCCTCTCCTCCCCTGGGCAGAAGTGGCCATGCCACCCTGTTTCGCTAAA
 2000                                                      2030
GCCCAACCTCCTGACCTGTCACCGTGAGCAGCTTTGGAAACAGGACCACAAAAATGAAAGCATGTCTCAATAGTA
           2100
AAAGAAACAAGAGATCTTTCAGGAAAGACGGATTGCATTAGAAATAGACAGTATATTTATAGTCACAAGGGCCCA
   2150                                                   2200
GCAGGGCTCAAAGTGGGGCAGGCTGGCTGGCCCGTCATGTCCTCAAAAGCGCCCTTGACGTCAAGTCTCCTTC
                2250
CCCTTTCCCCACTCCCTGGCTCTCAGAAGGTATTCCTTTTGAGTACAGTGTGTAAAGTGTAAATCCTTTTCTTT
                                              2350
ATTGTATCATTTGAACAACTAGGCTTCAGCATATTTATAGCGATCCATCGTTAGTTTTACTTTCCGTTGCCACA
 2400                                                  2450
ACCCTGTTTTATACCGTACTTAATAAATTCGGATATATTTTTCACAGTTTTTCCAAAAAAAAAAAAA
 2500
```

FIG. 17A

```
CCCCCCCCCGATGTAAGTCAACAACATCCTGGATTGGGACCCACTTTCTGGGCACTGCTGGCCAGTCCCAAA MET
                                                                      ATG
 80
GLU HIS LYS GLU VAL VAL LEU LEU LEU LEU PHE LEU LYS SER GLY GLN GLY GLU PRO
GAA CAT AAG GAA GTG GTT CTT CTA CTT TTA TTT CTG AAA TCA GGT CAA GGA GAG CCT
140
LEU ASP ASP TYR VAL ASN THR GLN GLY ALA SER LEU PHE SER VAL THR LYS LYS GLN LEU
CTG GAT GAC TAT GTG AAT ACC CAG GGG GCT TCA CTG TTC AGT GTC ACT AAG AAG CAG CTG
200
GLY ALA GLY SER ILE GLU GLU CYS ALA ALA LYS CYS GLU GLU ASP GLU GLU PHE THR CYS
GGA GCA GGA AGT ATA GAA GAG TGT GCA GCA AAA TGT GAG GAC GAG GAA TTC ACC TGC
260
ARG ALA PHE GLN TYR HIS SER LYS GLU GLN GLN CYS VAL ILE MET ALA GLU ASN ARG LYS
AGG GCA TTC CAA TAT CAC AGT AAA GAG CAA CAA TGT GTG ATA ATG GCT GAA AAC AGG AAG
320
SER SER ILE ILE ILE ARG MET ARG ASP VAL VAL LEU PHE GLU LYS LYS VAL TYR LEU SER
TCC TCC ATA ATC ATT AGG ATG AGA GAT GTA GTT TTA TTT GAA AAG AAA GTG TAT CTC TCA
380
GLU CYS LYS THR GLY ASN GLY LYS ASN TYR ARG GLY THR MET SER LYS THR LYS ASN GLY
GAG TGC AAG ACT GGG AAT GGA AAG AAC TAC AGA GGG ACG ATG TCC AAA ACA AAA AAT GGC
```

FIG. 17B

```
440
ILE THR CYS GLN LYS TRP SER SER THR PRO HIS ARG PRO ARG PHE SER PRO ALA THR
ATC ACC TGT CAA AAA TGG AGT TCC ACT TCT CCC CAC AGA CCT AGA TTC TCA CCT GCT ACA

500
HIS PRO SER GLU GLY LEU GLU GLU ASN TYR CYS ARG ASN PRO ASP ASN PRO GLN GLY
CAC CCC TCA GAG GGA CTG GAG GAG AAC TAC TGC AGG AAT CCA GAC AAC CCG CAG GGG

560
PRO TRP CYS TYR THR THR ASP PRO GLU LYS ARG TYR ASP TYR CYS ASP ILE LEU GLU CYS
CCC TGG TGC TAT ACT ACT GAT CCA GAA AAG AGA TAT GAC TAC TGC GAC ATT CTT GAG TGT

620
GLU GLU CYS MET HIS CYS SER GLY GLU ASN TYR ASP GLY LYS ILE SER LYS THR MET
GAA GAG TGT ATG CAT TGC AGT GGA GAA AAC TAT GAC GGC AAA ATT TCC AAG ACC ATG

680
SER GLY LEU GLU CYS GLN ALA TRP ASP SER GLN SER PRO HIS ALA HIS GLY TYR ILE PRO
TCT GGA CTG GAA TGC CAG GCC TGG GAC TCT CAG AGC CCA CAC GCT CAT GGA TAC ATT CCT

740
SER LYS PHE PRO ASN LYS LYS ASN LEU LYS LYS ASN TYR CYS ARG ASN PRO ASP ARG GLU LEU
TCC AAA TTT CCA AAC AAG AAG AAT CTG AAG AAG AAT TAC TGT CGT AAC CCC GAT AGG GAG CTG

800
ARG PRO TRP CYS PHE THR THR ASP PRO ASN LYS ARG TRP GLU LEU CYS ASP ILE PRO ARG
CGG CCT TGG TGT TTC ACC ACC GAC CCC AAC AAG CGC TGG GAA CTT TGC GAC ATC CCC CGC
```

FIG. 17C

```
860
CYS THR THR PRO PRO SER SER GLY PRO THR TYR GLN CYS LEU LYS GLY THR GLY GLU
TGC ACA ACA CCT CCA CCA TCT TCT GGT CCC ACC TAC CAG TGT CTG AAG GGA ACA GGT GAA

920
ASN TYR ARG GLY ASN VAL ALA VAL THR VAL SER GLY HIS THR CYS GLN HIS TRP SER ALA
AAC TAT CGC GGG AAT GTG GCT GTT ACC GTT TCC GGG CAC ACC TGT CAG CAC TGG AGT GCA

980
GLN THR PRO HIS THR HIS ASN ARG THR PRO GLU ASN PHE PRO CYS LYS ASN LEU ASP GLU
CAG ACC CCT CAC ACA CAT AAC AGG ACA CCA GAA AAC TTC CCC TGC AAA AAT TTG GAT GAA

1040
ASN TYR CYS ARG ASN PRO ASP GLY LYS ARG ALA PRO TRP CYS HIS THR THR ASN SER GLN
AAC TAC TGC CGC AAT CCT GAC GGA AAA AGG GCC CCA TGG TGC CAT ACA ACC AAC AGC CAA

1100
VAL ARG TRP GLU TYR CYS LYS ILE PRO SER CYS ASP SER SER PRO VAL SER THR GLU GLN
GTG CGG TGG GAG TAC TGT AAG ATA CCG TCC TGT GAC TCC TCC CCA GTA TCC ACG GAA CAA

1160
LEU ALA PRO THR ALA PRO PRO GLU LEU THR PRO VAL VAL GLN ASP CYS TYR HIS GLY ASP
TTG GCT CCC ACA GCA CCA CCT GAG CTA ACC CCT GTG GTC CAG GAC TGC TAC CAT GGT GAT

1220
GLY GLN SER TYR ARG GLY THR SER SER THR THR THR THR GLY LYS LYS CYS GLN SER TRP
GGA CAG AGC TAC CGA GGC ACA TCC TCC ACC ACC ACA GGA AAG AAG TGT CAG TCT TGG
```

FIG. 17D

```
1280
SER SER MET THR PRO HIS GLN LYS THR PRO GLU ASN TYR PRO ASN ALA GLY LEU
TCA TCT ATG ACA CCA CAC CAG AAG ACC CCA GAA AAC TAC CCA AAT GCT GGC CTG

1340
THR MET ASN TYR CYS ARG ASN PRO ASP ALA ASP LYS GLY PRO TRP CYS PHE THR THR ASP
ACA ATG AAC TAC TGC AGG AAT CCA GAT GCC GAT AAA GGC CCC TGG TGT TTT ACC ACA GAC

1400
PRO SER VAL ARG TRP GLU TYR CYS ASN LEU LYS LYS CYS SER GLY THR GLU ALA SER VAL
CCC AGC GTC AGG TGG GAG TAC TGC AAC CTG AAA AAA TGC TCA GGA ACA GAA GCG AGT GTT

1460
VAL ALA PRO PRO VAL LEU LEU PRO ASP VAL GLU THR PRO SER GLU GLU ASP CYS
GTA GCA CCT CCG GTT GTC CTT CCA GAT GTA GTA GAG ACT CCT TCC GAA GAA GAC TGT

1520
MET PHE GLY ASN GLY LYS GLY TYR ARG GLY LYS ARG ALA THR THR VAL THR GLY THR PRO
ATG TTT GGG AAT GGG AAA GGA TAC CGA AAG AGG GCG ACC ACT GTT ACT GGG ACG CCA

1580
CYS GLN ASP TRP ALA ALA GLN GLU PRO HIS ARG HIS SER ILE PHE THR PRO GLU THR ASN
TGC CAG GAC TGG GCT GCC CAG GAG CCC CAT AGA CAC AGC ATT TTC ACT CCA GAG ACA AAT

1640
PRO ARG ALA GLY LEU GLU LYS ASN TYR CYS ARG ASN PRO ASP GLY ASP VAL GLY GLY PRO
CCA CGG GCG GGT CTG GAA AAA AAT TAC TGC CGT AAC CCT GAT GGT GAT GTA GGT GGT CCC
```

FIG. 17E

```
1700
TRP CYS TYR THR THR ASN PRO ARG LYS LEU TYR ASP TYR CYS ASP VAL PRO GLN CYS ALA
TGG TGC TAC ACG ACA AAT CCA AGA AAA CTT TAC GAC TAC TGT GAT GTC CCT CAG TGT GCG

1760
ALA PRO SER PHE ASP CYS GLY LYS PRO GLN VAL GLU PRO LYS LYS CYS PRO GLY ARG VAL
GCC CCT TCA TTT GAT TGT GGG AAG CCT CAA GTG GAG CCG AAG AAA TGT CCT GGA AGG GTT

1820
VAL GLY GLY CYS VAL ALA HIS PRO HIS SER TRP PRO TRP GLN VAL SER LEU ARG THR ARG
GTG GGG GGG TGT GTG GCC CAC CCA CAT TCC TGG CCC TGG CAA GTC AGT CTT AGA ACA AGG

1880
PHE GLY MET HIS PHE CYS GLY GLY THR LEU ILE SER PRO GLU TRP VAL LEU THR ALA ALA
TTT GGA ATG CAC TTC TGT GGA GGC ACC TTG ATA TCC CCA GAG TGG GTG TTG ACT GCT GCC

1940
HIS CYS LEU GLU LYS SER PRO ARG PRO SER SER TYR LYS VAL ILE LEU GLY ALA HIS GLN
CAC TGC TTG GAG AAG TCC CCA AGG CCT TCA TCC TAC AAG GTC ATC CTG GGT GCA CAC CAA

2000
GLU VAL ASN LEU GLU PRO HIS VAL GLN GLU ILE GLU VAL SER ARG LEU PHE LEU GLU PRO
GAA GTG AAT CTC GAA CCG CAT GTT CAG GAA ATA GAA GTG TCT AGG CTG TTC TTG GAG CCC

2060
THR ARG LYS ASP ILE ALA LEU LEU LYS LEU SER SER PRO ALA VAL ILE THR ASP LYS VAL
ACA CGA AAA GAT ATT GCC TTG CTA AAG CTA AGC AGT CCT GCC GTC ATC ACT GAC AAA GTA
```

FIG. 17G

```
2420
LEU GLY CYS ALA ARG PRO ASN LYS PRO GLY VAL TYR VAL ARG VAL SER ARG PHE VAL THR
CTT GGC TGT GCA CGC CCC AAT AAG CCT GGT GTC TAT GTT CGT GTT TCA AGG TTT GTT ACT

2480
TRP ILE GLU GLY VAL MET ARG ASN ASN ××× TTGGACGGGAGACAGAGTGACGCACTGACTCACTAGAG
TGG ATT GAG GGA GTG ATG AGA AAT AAT TAA

2549
GCTGGGACGTGGGTAGGGATTAGCATGCTGGAAATAACTGGCAGTAATCAAACGAAGACACTGTCCCCAGCTACCAGCT

2629
ACGCCAAACCTCGGCCATTTTTGTGTATTTTCTGACTGCTGGATTCTGTAGTAAGGTGACATAGCTATGAA

2709
AAAATAAACTCTGTACTTAACTTTGATTTGAGTAAATTTTGGTTTTGGTCTTCAACAAAAAAAAAAAAAAA
```

HYBRID PROTEINS OF HUMAN PLASMINOGEN AND HUMAN T-PA, PHARMACEUTICAL COMPOSITIONS AND METHODS OF TREATMENT

This application is a continuation of application 07/808979 filed Dec. 17, 1991, now abandoned, which is a continuation of application 07/212,910 filed Jun. 29, 1988, now abandoned.

The present invention relates to a hybrid fibrinolytic enzyme, its preparation, pharmaceutical compositions containing it and its use in the treatment of thrombotic disease, and to enzyme derivatives for use in the treatment of thromboembolic diseases, in particular acute myocardial infarction.

European Patent No 0,009,879 discloses derivatives of in vivo fibrinolytic enzymes which are useful therapeutic agents for treating venous thrombosis. The derivatives are characterised by the active catalytic site on the enzymes being blocked by a group which is removable by hydrolysis such that the pseudo first order rate constant for hydrolysis is in the range $10^{-6}$ to $10^{-3}$ $sec^{-1}$.

EP-0155387 discloses fibrinolytically active hybrid protein which comprises one chain of a 2-chain protease linked to a chain of a different 2-chain protease, or to the same chain of the same protease, at least one of the chains in the hybrid protein being derived from a fibrinolytically active protease, such that the hybrid protein has a catalytic site essential for fibrinolytic activity which is optionally blocked by a removable blocking group.

Examples of the hybrid protein include plasmin A-chain linked to tissue-type plasminogen activator (t-PA) B-chain or urokinase B-chain.

The hybrid proteins may be prepared by mixing a chain of one protease with a chain of another protease, optionally with dialysis, under oxidative conditions.

Alternatively, the hybrid proteins may be prepared by taking the genetic information (DNA sequence) of each protein, cutting and ligating this to construct a new DNA sequence coding for the hybrid protein, and expressing this DNA in prokaryote or eukaryote hosts.

The sequence of amino acids making up the enzyme tissue-type plasminogen activator (t-PA) and the nucleotide sequence for the cDNA which codes for t-PA are known (see Pennica et al., 1983; Nature, 301, 214). t-PA is known to have fibrinolytic activity.

As used herein, the term tissue-type plasminogen activator (t-PA) denotes a plasminogen activator of the group having the immunological properties defined for t-PA at the XXVIII Meeting of the International Committee on Thrombosis and Haemostasis, Bergamo, Italy, 27 July 1982.

The amino acid sequence of various forms of t-PA are known. The abovementioned Nature 1983 reference discloses the sequence for the L-chain and the mature S-chain forms of t-PA, also discussed by Vehar et al., Biotechnology, 1984, 2, 1051-7 in which the processing of initially formed t-PA by removal of a pro-sequence to give the S-chain form is reported. Pohl et al., FEBS letters, 1984, Vol. 168 No.1, 29-32, refers to the N-terminal multiplicity of t-PA and discloses the Unchain form. The numbering system for the amino acid sequence of t-PA used herein is that described in the Nature 1983 reference for mature (S-chain) t-PA in which the N-terminal serine is numbered 1. By this system, L-chain t-PA has an N-terminal glycine residue at position -3 and U-chain t-PA has an N-terminal valine at position 4. References to t-PA herein are understood to include all such variant forms.

Native t-PA is composed of a B or light (L) and an A or heavy (H) chain. The B-chain contains the active site of the enzyme. The cleavage site for the conversion of t-PA from the single to the two-chain form is located between residues arg-275 and ile-276. In the two-chain form the chains are held together by a disulphide bridge formed between residues cys-264 in the A-chain and cys-395 in the B-chain.

It has been shown (Ny, T. et al, 1984; Proc. Natl. Acad. Sci. U.S.A., 81, 5355) that the A chain exhibits a number of structural and functional domains which are homologous to structures found in other plasma proteins: two triple disulphide-bonded structures or kringles, a growth-factor-like domain and a fibronectin-finger-like domain.

The region from amino acid residues 44 to 91 has been termed the "growth factor domain" (Banyai, L., et al FEBS Lett. 163, 37, 1983). The genetic information which codes for the major part of this domain, residues 51 to 86 inclusive, and partially codes for residues 50 and 87, lies on a single exon. The region from the first to last cysteine residues within this region, residues 51 to 84 inclusive, defines a triple-disulphide linked structure which will be referred to herein as the t-PA growth factor domain.

Fibronectin has twelve finger-domains per monomer, responsible for fibrin-affinity (Eur. J. Biochem. 154, 15-29 (1986)). The amino acid sequences of these finger domains are known (EMBO J.4, 1755-1759 (1985); Eur. J. Biochem. 128, 605-623 (1982); Proc. Natl. Acad. Sci. USA 80., 137-141 (1983)). It has been shown (J. Biol. Chem. 260, 5328-5341 and 13666-13676 (1985)) that part of Factor XII shows structural homology with the finger-domains of fibronectin. It has also been shown (Bányai, L. et al, 1983; FEBS Lett., 163, 37)that a part of the t-PA enzyme shows structural homology with the finger-domains of fibronectin. This region from amino acid residue 6 to 43 has been termed the t-PA finger domain. The genetic information for this domain lies on a single exon (Ny, T. et al, 1984; Proc. Natl. Acad. Sci. U.S.A., 81, 5355). The term "finger domain" will be used hereinafter to refer to an amino acid sequence showing structural homology with the finger-domains of fibronectin, or the sequence of a fibronectin finger-domain itself.

The sequence of amino acids making up the enzyme urokinase-type plasminogen activator (u-PA) in its single chain and two chain forms (Verstraete, M. and Collen, D., 1986; Blood, 67, 1529) and the nucleotide sequence for the cDNA which codes for human u-PA (Holmes, W. E. et al, 1985; Bio/technology 3, 923-929) are known. Urokinase-type plasminogen activator is known to have fibrinolytic activity. The two chains of u-PA are termed the A- and B-chain. The B-chain contains the active site of the enzyme. The cleavage site for the conversion of u-PA from the single to the two chain form is located between residues lys-158 and ile-159. In the two chain form the chains are held together by a disulphide bridge formed between residues cys-148 in the A-chain and cys-279 in the B-chain.

As used herein, the term urokinase-type plasminogen activator (u-PA) denotes a plasminogen activator of the group having the immunological properties defined for u-PA at the XXVIII meeting of the International Committee on Thrombosis and Haemostasis, Bergamo, Italy, 27 July 1982.

The numbering system for the amino acid and nucleotide sequence of u-PA used herein is that described in Holmes, W. E. et al, 1985 (op. cit.) in which the N-terminal serine residue is numbered 1.

In addition to the native forms of t-PA and u-PA described above, various muteins are also known, see for example EP-A-0201153, EP-A-0233013, EP-A-0199574, WO 86/01538, EP-A-0227462, EP-A-0253582, WO 86/04351, EP-A-0236040, EP-A-0200451, EP-A-0238304, EP-0225286, DE 3537176, WO 87/04722 and EP-A-0236289.

Thus, EP-A-0201153 discloses at page 1, lines 30-35, a modified tissue-type plasminogen activator comprising an amino acid without a charged side chain in place of lysine at position 277. In a preferred aspect, the amino acid without a charged side chain is isoleucine.

EP-A-0233013 discloses in claim 1 on page 10 thereof a modified tissue-type plasminogen activator comprising an amino acid other than arginine or lysine at position 275. In claim 2, the amino acid is disclosed as histidine, threonine, serine, asparagine, aspartic acid or glutamic acid.

EP-A-0199574 discloses in claim 7 a single-chain human tissue plasminogen activator (t-PA) mutant produced by recombinant host cells, and resistant to specific enzyme cleavage, which is stabilized in single-chain form by site directed mutagenesis at a two-chain cleavage site, wherein the two-chain activation site is disposed in the range of residues 270 through 279 of t-PA and the site directed mutagenesis is accomplished by substitution of at least one amino acid residue within the two-chain activation site.

International Application WO 86/01538 discloses at page 4, lines 26-32 a modified t-PA characterized by the formula t-PA (Lys 277→X), wherein X is selected from the group consisting of one or more amino acid substitutions, modifications or deletions that prevents any substantial complexation between amino acid 277 and amino acid 194 in the single chain form of that t-PA.

EP-A-0227462 discloses in claim 1 polypeptides having tissue plasminogen activator activity in dissolving clots, having a specific activity at least 0.3 of the specific activity of natural tissue plasminogen activator and at least one improved property as to specific activity, fibrin dependence of activity, or inhibitor susceptibility, as a result of reducing the number of glycosylation sites; deletion of at least three amino acids at the C-terminus; or substitution of an amino acid at the cleavage site, in a naturally occurring polypeptide having tissue plasminogen activator activity. At page 3, lines 3-7, EP-A-0227462 states that the novel polypeptides involve changes at least one glycosylation site, at least one change at the cleavage site in the region from 272 to 280, particularly in the sequence Phe$_{274}$-Arg$_{275}$-Ile$_{276}$-Lys$_{277}$ (FRIK).

EP-A-0225286 discloses at page 6, line 29 to page 7, line 15 human t-PA proteins having the formula

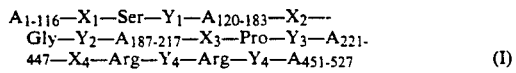

$$A_{1-116}—X_1—Ser—Y_1—A_{120-183}—X_2—$$
$$Gly—Y_2—A_{187-217}—X_3—Pro—Y_3—A_{221-}$$
$$447—X_4—Arg—Y_4—Arg—Y_4—A_{451-527} \quad (I)$$

in which $A_{1-116}$ represents the N-terminal amino acid sequence consisting of amino acids 1 to 116 of mature t-Pa, $A_{120-183}$ represents the amino acid sequence consisting of amino acids 120 to 183 of mature t-PA, $A_{187-217}$ represents the amino acid sequence consisting of amino acids 187 to 217 of mature t-PA, $A_{221-447}$ represents the amino acid sequence consisting of amino acids 221 to 447 of mature t-PA, $A_{451-527}$ represents the C-terminal amino acid sequence consisting of amino acids 451 to 527 of mature t-PA, $X_1$, $X_2$, $X_3$ and $X_4$ each represent Asn or another genetically encoded amino acid, $Y_1$, $Y_2$ and $Y_3$ each represent Ser or another genetically encoded amino acid other than Thr and $Y_4$ represents Thr or another genetically encoded amino acid other than Ser, in the one-chain or in the two-chain form, provided that at least one of the radicals $X_1$, $X_2$, $X_3$ and $X_4$ is different from Asn and/or at least one of radicals $Y_1$, $Y_2$, $Y_3$ and $Y_4$ is different from Ser and Thr.

De 3527176 discloses, in the Derwent Abstract thereof, the production of a tissue plasminogen activator in yeast to obtain new polypeptides with t-PA activity containing a glutamine residue in one of positions 117, 184, 218 and 448 of the amino acid sequence.

International Application WO 87/04722 discloses in claim 1 a thrombolytic protein having tissue plasminogen activator type activity characterized by a peptide sequence substantially the same as the peptide sequence of human t-PA, wherein (a) Arg-275 is deleted or is replaced by a different amino acid, and (b) at least one of the consensus N-linked glycosylation sites is modified to other than a consensus N-linked glycosylation site.

References herein to T-PA and u-PA species include both native forms and muteins.

Plasmin is a two-chain serine protease which may be obtained by the cleavage of the single chain precursor, plasminogen, at a specific internal peptide bond. The amino acid sequence of human plasminogen is known (Wiman and Walters (1975) Eur. J. Biochem. 50, 489-494 and 58, 539-547; Wiman (1977) Eur. J. Biochem. 76, 129-137; Sottrup-Jensen et al. (1978) Fibrinolysis and Thrombolysis Vol. 3, 191-209, Raven Press, New York; and Sottrup-Jensen et al. (1978) Atlas of Protein Sequence and Structure Vol. 5, Suppl. 3, p 91, National Biomedical Research Foundation, Silver Spring, Md.). A partial nucleotide sequence coding for amino acid residues 272-790 of human plasminogen has also been described (Malinowski, D. P. et al., 1984, Biochemistry, 23, 4243-4250). The cleavage site of human plasminogen is located between residues arg-560 and val-561 (according to the sequence numbering of Sottrup-Jensen et al. (1978) Atlas of Protein Sequence (op.cit.)). Two species of plasminogen have been identified (F. J. Castellino, Chemical Reviews vol. 81 p431 (1981)): glu$_1$ which has an N-terminal glutamic acid residue at position 1 and lys$_{77}$ which has an N-terminal lysine residue at position 77. Glu-plasminogen is also easily converted by limited plasmic digestion to other modified forms with N-terminal valine (val$_{78}$) or methionine (met$_{68}$) (C. Miyashita, E. Wenzel and M. Heiden, Haemostasis 18, suppl.1 pp 7-13 (1988)). References to plasminogen herein are understood to include all these species.

Recently a complete nucleotide sequence has been described (Forsgren, M., et al., 1987, FEBS Letters 213, 254-260). The nucleotide sequence predicts the existence of an extra, previously unreported, isoleucine residue near the N-terminus of the A-chain. This finding has been independently confirmed (McLean, J. N., et al., 1987, Nature 330, 132-137). Accordingly all sequence numbering (amino acid and nucleotide) below follows Forsgren et al. (1987). In this numbering sequence the plasminogen cleavage site is located between residues arg-561 and val-562 and the N-terminal modified forms are termed $met_{69}$, $lys_{78}$ and $val_{79}$.

Plasminogen has five kringle structures. The region from the first to the last cysteine residue of each kringle structure, residues 84 to 162, 166 to 243, 256 to 333, 358 to 435 and 462 to 541 inclusive will be referred to herein as the $K_1P$, $K_2P$, $K_3P$, $K_4P$ and $K_5P$ domains respectively.

According to the present invention there is provided a hybrid plasminogen activator which comprises the five kringle domains of plasminogen linked to the B-chain of t-PA or u-PA via an amino acid sequence comprising, respectively, the t-PA cleavage site between residues 275 and 276 and the cysteine residue 264 of t-PA or the u-PA cleavage site between residues 158 and 159 and the cysteine residue 148 of u-PA.

It will be understood that by the term 'B-chain' is meant at least that portion of the B-chain containing the functional active centre of t-PA or u-PA, and preferably comprises residues 276-527 or 159-411 respectively.

The linking sequence of amino acids may be introduced synthetically during the preparation of the hybrid plasminogen activator (PA) and/or derived from native sequences.

Native plasminogen includes cysteine residues at positions 548 and 558, C-terminal to plasminogen kringle 5, which participate in the interchain disulphide bridges of the two-chain plasmin form. In the preferred embodiment these residues are not present in the linking sequence.

It will be appreciated that to prevent cleavage of the plasminogen kringles from the t-PA or u-PA B-chain in vivo, the linking sequence should be chosen so as to avoid the presence of a site susceptible to trypsin-like proteolytic cleavage N-terminal to residue cys-264 of t-PA or cys-148 of u-PA, as appropriate.

Where the B-chain of t-PA is employed, the linking sequence of amino acids preferably comprises t-PA residues 264 to 275 inclusive, more preferably residues 262 to 275 inclusive.

Where the B-chain of u-PA is employed, the linking sequence of amino acids preferably comprises u-PA residues 148 to 158 inclusive, more preferably residues 137 to 158 inclusive.

In one preferred aspect, the hybrid PA may be represented symbolically as:

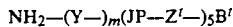

where $B^t$ comprises residues 276–527 of t-PA, m is 0 or 1, preferably 1, each of the 5 values of KP represents a kringle domain derived from plasminogen in sequence and Y and each of the 5 values of $Z^t$ independently represents a bond or a linking sequence of amino acids which may be introduced synthetically during the preparation of the hybrid PA and/or derived from native plasminogen and/or t-PA sequences, the sequence $Z_5^t$ comprising at least residues cys-264 and arg-275 of t-PA.

In a second preferred aspect, the hybrid PA may be represented symbolically as:

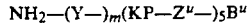

where $B^u$ comprises residues 159-411 of u-PA, Y and each of the 5 values of $Z^u$ independently represents a bond or a linking sequence of amino acids which may be introduced synthetically during the preparation of the hybrid PA and/or derived from native plasminogen and/or u-PA sequences, the sequence $Z_5^u$ comprising at least residues cys-148 ana lys-158 of u-PA and m and each of the 5 values of KP are as previously defined.

When m is 1, the sequence Y may take one of the values found in various forms of native plasminogen, such as the $glu_1$ or $lys_{78}$ forms, that is plasminogen residues 1 to 83 or 78 to 83 respectively.

Optionally, as taught generally in EP-A-0241210, the sequence Y may commence with one or more finger domains, defined herein as an amino acid sequence showing structural homology with the finger-domains of fibronectin, such as a fibronectin finger domain itself or a t-PA finger domain, preferably a t-PA finger domain.

Where a finger domain is derived from t-PA, the finger domain sequence may optionally extend at the N-terminus to include residues preceding residue 6 of native t-PA, such as residues 4 and 5, 1 to 5 or −3 to 5 respectively of the U-, S- or L-chain forms of native t-PA. The finger domain sequence preferably extends at the N-terminus to comprise residues 1 to 5 of native t-PA.

Each finger domain sequence may optionally be linked to a second sequence of amino acids which corresponds to the growth-factor domain of native t-PA. Thus, representing the finger domain sequence (for example residues 6 to 43 of t-PA) as F and the growth-factor domain sequence (residues 51 to 84 of t-PA) as G, Y comprises one or more N-terminal units of the form $A—F—X_1—$ and/or $A—F—X_2—G—X_3—$, where $X_1$, $X_2$ and $X_3$ represent bonds or linking sequences of amino acids which may be introduced synthetically during the preparation of the hybrid PA and/or be derived from native t-PA sequences adjacent the F and G domains and A is an optional N-terminal extension of the F domain.

In a preferred aspect, the linking sequence $X_1$ comprises amino acid residues selected from the residues 44 to 50 and 85 to 91, and more preferably comprises residues 44 to 50 and 88 to 91, of native t-PA, optionally linked at the C-terminus to a sequence of amino acids, such as -pro-gly-. The linking sequence $X_2$ preferably comprises residues selected from the residues 44 to 50 of native t-PA, and more preferably comprises residues 44 to 50. The linking sequence $X_3$ preferably comprises residues selected from the residues 85 to 91 of native t-PA and more preferably comprises residues 85 to 91, optionally linked at the C-terminus to a sequence of amino acids such as -pro-gly-.

It will be appreciated that to prevent cleavage of the additional domain(s) from one another or from the remainder of the hybrid plasminogen activator in vivo, inter-domain linking sequences and linking sequences between the additional domain(s) and the plasminogen activator molecule should be chosen so as to avoid the presence of a site susceptible to proteolytic cleavage. Thus, in particular, the linking sequence $X_1$ or $X_3$ will preferably end with a residue other than arginine or lysine.

Y preferably comprises up to 6 additional finger domains, more preferably up to 2, most preferably 1, each of which may optionally be linked to a growth factor domain.

$Z_1$, $Z_2$, $Z_3$ and $Z_4$ preferably represent the native plasminogen inter-domain sequences between plasminogen kringle domains 1 and 2, 2 and 3, 3 and 4 and 4 and 5, respectively.

Suitable sequences ($Z_5^t$) linking the C-terminal plasminogen kringle domain to the t-PA B-chain include:

| | |
|---|---|
| [AAPSTCGLRQYSQPQFR] | 1. |
| [AAPSTCGLRQYSQPQFQ] | 2. |
| [STCGLRQYSQPQFR] | 3. |

(single letter amino acid notation) from which it can be seen that the sequences 1 and 2 consist of residues 542-544 of plasminogen and residues 263 to 275 of t-PA linked by a serine residue. The interposed serine residue can be identified with ser-545 of plasminogen or ser-262 of t-PA. In sequence 2, residue 275 of t-PA has been replaced by glutamine in accordance with EP-A-0233013. Sequence 3 consists of residues 262 to 275 of t-PA.

The preferred sequence ($Z_5^u$) linking the C-terminal plasminogen kringle domain to the u-PA B-chain is:

(AAPSFPSSPPEELKFQCGQKTLRPRFK]

(single letter amino acid notation) from which it can be seen that the sequence consists of residues 542-546 of plasminogen and residues 137 to 158 of u-PA.

The preferred hybrid PA's of the invention have the following structures:

| | |
|---|---|
| Plg 1-541[AAPSTCGLRQYSQPQFR]B' | 1. |
| Plg 1-541[AAPSTCGLRQYSQPQFQ]B' | 2. |
| Plg 1-541 [STCGLRQYSQPQFR]B' | 3. | where Plg 1-541 represents residues 1-541 of plasminogen (that is, including kringles 1 to 5), B' is as previously defined and the symbols in brackets represent amino acid residues according to the single letter amino acid notation, including one and two chain variants, lys$_{78}$ and glu$_1$ variants, and mixtures thereof.

The hybrid PA of the invention may be derivatised to provide pharmaceutically useful conjugates analogous to known PA-containing conjugates, for example:

(a) an enzyme-protein conjugate as disclosed in EP-A-0 155 388, in which the catalytic site on the enzyme which is responsible for fibrinolytic activity is blocked by a human protein attached thereto by way of a reversible linking group;

(b) an enzyme-protein conjugate as disclosed in EP-A-0 152 736, comprising at least one optionally blocked fibrinolytic enzyme linked by way of a site other than the catalytic site responsible for fibrinolytic activity to at least one human protein;

(c) a protein-polymer conjugate as disclosed in EP-A-0183503 comprising a pharmaceutically useful protein linked to at least one water soluble polymer by means of a reversible linking group; or (d) an enzyme conjugate as disclosed in EP-A-0184363 comprising a plurality of fibrinolytic enzymes linked together through the active centres thereof by means of a removable blocking group.

The hybrid PA of the invention may take the place of a PA as the enzyme or (human) protein component, as appropriate, of any of the conjugates described above.

The above mentioned derivatives of the hybrid PA may be used in any of the methods and compositions described hereinafter for the hybrid PA itself.

In a further aspect, the invention provides a process for preparing hybrid plasminogen activator according to the invention which process comprises expressing DNA encoding said hybrid plasminogen activator in a recombinant host cell and recovering the hybrid plasminogen activator product.

The DNA polymer comprising a nucleotide sequence that encodes the hybrid PA also forms part of the invention.

The process of the invention may be performed by conventional recombinant techniques such as described in Maniatis et. al., Molecular Cloning—A Laboratory Manual; Cold Spring Harbor, 1982 and DNA Cloning vols I, II and III (D. M. Glover ed., IRL Press Ltd).

In particular, the process may comprise the steps of:
i) preparing a replicable expression vector capable, in a host cell, of expressing a DNA polymer comprising a nucleotide sequence that encodes said hybrid plasminogen activator;
ii) transforming a host cell with said vector;
iii) culturing said transformed host cell under conditions permitting expression of said DNA polymer to produce said hybrid plasminogen activator; and
iv) recovering said hybrid plasminogen activator.

The invention also provides a process for preparing the DNA polymer by the condensation of appropriate mono-, di- or oligomeric nucleotide units.

The preparation may be carried out chemically, enzymatically, or by a combination of the two methods, in vitro or in vivo as appropriate. Thus, the DNA polymer may be prepared by the enzymatic ligation of appropriate DNA fragments, by conventional methods such as those described by D. M. Roberts et al in Biochemistry 1985, 24, 5090-5098.

The DNA fragments may be obtained by digestion of DNA containing the required sequences of nucleotides with appropriate restriction enzymes, by chemical synthesis, by enzymatic polymerisation, or by a combination of these methods.

Digestion with restriction enzymes may be performed in an appropriate buffer at a temperature of 20°-70° C., generally in a volume of 50μl or less with 0.1-10 μg DNA.

Enzymatic polymerisation of DNA may be carried out in vitro using a DNA polymerase such as DNA polymerase I (Klenow fragment) in an appropriate buffer containing the nucleoside triphosphates DATP, DCTP, DGTP and DTTP as required at a temperature of 10°-37° C., generally in a volume of 50 μl or less.

Enzymatic ligation of DNA fragments may be carried out using a DNA ligase such as T4 DNA ligase in an appropriate buffer at a temperature of 4° C. to ambient, generally in a volume of 50 μl or less.

The chemical synthesis of the DNA polymer or fragments may be carried out by conventional phosphotriester, phosphite or phosphoramidite chemistry, using solid phase techniques such as those described in 'Chemical and Enzymatic Synthesis of Gene Fragments—A Laboratory manual' (ed. H. G. Gassen and A. Lang), Verlag Chemie, Weinheim (1982),or in other scientific publications, for example M. J. Gait, H. W. D. Matthes, M. Singh, B. S. Sproat, and R. C. Titmas, Nucleic Acids Research, 1982, 10, 6243; B. S. Sproat and W. Bannwarth, Tetrahedron Letters, 1983, 24, 5771; M. D. Matteucci and M. H Caruthers, Tetrahedron Letters, 1980, 21, 719; M. D. Matteucci ana M. H. Caruthers, Journal of the American Chemical Society, 1981, 103, 3185; S. P. Adams et al., Journal of the American Chemical Society, 1983, 105, 661; N. D. Sinha, J. Biernat, J. McMannus, and H. Koester, Nucleic Acids Research, 1984, 12, 4539; and H. W. D. Matthes et al., EMBO Journal, 1984, 3, 801. Preferably an automated DNA synthesizer is employed.

The DNA polymer is preferably prepared by ligating two or more DNA molecules which together comprise a DNA sequence encoding the hybrid PA.

The DNA molecules may be obtained by the digestion with suitable restriction enzymes of vectors carrying the required coding sequences.

The precise structure of the DNA molecules and the way in which they are obtained depends upon the structure of the desired hybrid PA product. The design of a suitable strategy for the construction of the DNA molecule coding for the hybrid PA is a routine matter for the skilled worker in the art.

In the preferred embodiment, the DNA molecule may conveniently be prepared by ligating a first DNA molecule encoding kringles 1 to 5 of plasminogen with one or more DNA molecules which, together with said first DNA molecule, encode the B-chain of t-PA or u-PA, such that the ligated molecule codes for the amino acid linking sequence comprising, respectively, the t-PA cleavage site between residues 275 and 276 and the cysteine residue 264 of t-PA or the u-PA cleavage site between residues 158 and 159 and the cysteine residue 148 of u-PA.

By way of example and guidance, two strategies for the construction of DNA molecules coding for two specific hybrid plasminogen activators are described below Strategy A The first DNA molecule may be obtained by the digestion of a first vector carrying the required part of the plasminogen coding sequence. Conveniently the native plasminogen sequence is modified to introduce a new NarI site 3' to the $K_5P$ coding region, preferably at nucleotide position 1758, and any NarI site formerly present in the vector is destroyed. The first vector preferably also carries at least part of the t-PA coding sequence including the SstI site at nucleotide position 1417 (Pennica et al., 1983, op. cit.) in the B-chain coding region and the portion of the B-chain coding region 3' thereof. Digestion of the first vector with restriction enzymes NarI and SstI thus provides a DNA molecule coding for plasminogen kringles 1 to 5 and part of the t-PA B-chain, and carrying vector functions.

A second DNA molecule may be obtained by the digestion of a second vector carrying the t-PA B-chain coding sequence. Digestion of the second vector with suitable restriction enzyme(s) such as BanII provides a DNA molecule coding for part of the t-PA B-chain. The Ban II sticky end is compatible with the SstI sticky end of the first DNA molecule.

The first and second DNA molecules are linked via an oligonucleotide linker having suitable sticky ends compatible with the NarI and BanII sticky ends of said DNA molecules, and having a structure such that, upon ligation of the first and second DNA molecules with the linker, the resulting molecule codes for an amino acid linking sequence comprising the t-PA cleavage site between residues 275–276 and the cysteine residue 264 of t-PA. Conveniently, the oligonucleotide linker has the following structure:

```
5' CG CCG TCG ACC TGC GGC CTG AGA CAG TAC AGC
3'    GGC AGC TGG ACG CCG GAC TCT GTC ATG TCG

CAG CCT CAG TTT CGC ATC AAA GGA GGG CT 3'
GTC GGA GTC AAA GCG TAG TTT CCT C      5'
```

The ligation of the first and second DNA molecules with the above linker may be carried out sequentially or, more preferably, in a single step. Legation of the BanII and SstI sticky ends of the molecules reforms the t-PA B-chain coding region. The resulting sequence at the reconstructed NarI site is believed to be as follows:

```
               NarI
5' . . . GCG G |CG  CCG TCG ACC TGC GGC CTG . . . 3'
3' . . . CGC C  GC| GGC AGC TGG ACG CCG GAC . . . 5'
         ala ala    pro ser* thr cys gly leu
         542 543    544      263 264 265 266
```

Amino acids marked 542–544 are the C-terminal residues of a peptide sequence comprising residues 1 to 544 of plasminogen. The serine residue marked * may be identified with serine 545 of plasminogen or serine 262 of t-PA. Amino acids marked 263–266 are the N-terminal residues of a peptide sequence comprising residues 263–527 of t-PA.

The said first vector carrying the required part of the plasminogen coding sequence, that is, kringles 1 to 5, and with a NarI site introduced at nucleotide position 1758, may conveniently be obtained by the digestion with restriction enzymes HindIII and AhaII and, separately, AhaII and DdeI of a vector carrying the plasminogen gene, in which any existing vector NarI site has been removed by conventional methods. The HindIII site is located in the 5' untranslated region, and the AhaII site at nucleotide position 1572 and the DdeI site at nucleotide position 1748 are in the kringle 5 coding region of the plasminogen gene. The HindIII-AhaII and AhaII-DdeI fragments may be ligated together and to an oligonucleotide linker having a DdeI sticky end, coding for the remainder of the kringle 5 coding region and containing a NarI site. The linker is preferably also provided with a BglII sticky end, such that the resulting DNA molecule, coding for plasminogen kringles 1 to 5, has a HindIII and a BglII sticky end and may be held in a suitable vector such as pTRE12 (EP-A-0 201 153) between the HindIII and BglII sites thereof, creating vector (A).

In order to introduce the part of the t-PA B-chain coding sequence which is 3' to the SstI site into the vector which carries the plasminogen $K_1P$-$K_5P$ coding region, the BglII fragment encoding the mature t-PA polypeptide obtained from a suitable vector (B) coding therefor, such as pTRE15 (EP-A-0 201 153), is inserted in the BglII site of the vector (A). The unwanted portion of the resulting vector may then be excised by digestion with restriction enzymes NarI and SstI to yield the said first DNA molecule encoding plasminogen kringles 1 to 5, t-PA B-chain 3' to the SstI site and vector functions.

The said second vector carrying the required part of the t-PA coding sequence, that is, the B-chain, may be for example a vector (B) encoding the mature t-PA polypeptide, such as pTRE15 (EP-A-0 201 153).

Strategy B

The first DNA molecule may be obtained by the digestion of a first vector carrying the required part of the plasminogen coding sequence. Conveniently the native plasminogen sequence is modified to introduce a new NarI site 3' to the $K_5P$ coding region, preferably at nucleotide position 1758, and any NarI site formerly present in the vector is destroyed. The first vector conveniently also has a BglII site positioned such that digestion of the first vector with restriction enzymes NarI and BglII provides a DNA molecule coding for plasminogen kringles 1 to 5 and carrying vector functions.

A second DNA molecule may be obtained by the digestion of a second vector carrying the u-PA B-chain coding sequence. Conveniently the native u-PA sequence is first modified by the introduction of an SstI site 5' to the u-PA B-chain coding region. The second vector preferably also carries at least part of the u-PA A-chain coding sequence 5' to the B-chain coding sequence and conveniently has a BglII site 3' to the B-chain coding sequence. Digestion of the second vector with restriction enzymes BglII and SstI thus provides a DNA molecule coding for u-PA B-chain and part of the A-chain.

The first and second DNA molecules are linked via an oligonucleotide linker having suitable sticky ends, preferably a 5' NarI sticky end and a 3' SstI sticky end, and having a structure such that, upon ligation of the first and second DNA molecules with the linker, the resulting molecule codes for an amino acid linking sequence comprising the u-PA cleavage site between residues 158 and 159 and the cysteine residue 148 of u-PA. Conveniently, the oligonucleotide linker has the following structure:

```
5' CG CCT TCA TTT CCC TCC TCT CCT CCA GAA GAG CT 3'
3'    GGA AGT AAA GGG AGG AGA GGA GGT CTT C       5'
```

The ligation of the first and second DNA molecules with the above linker may be carried out sequentially or, more preferably, in a single step. The resulting sequence at the reconstructed NarI and SstI sites is believed to be as follows:

N-terminal residues of a peptide sequence comprising residues 137–411 of u-PA.

The nucleotides marked * have been substituted for the native nucleotides in the course of creating the NarI and SstI restriction sites, without altering the encoded amino acids.

The said first vector carrying the required part of the plasminogen coding sequence, that is, kringles 1 to 5, and with a NarI site introduced at nucleotide position 1758, may conveniently be obtained as described in strategy A above.

The said second vector carrying the required part of the u-PA coding sequence, that is, the B-chain, and with an SstI site 5' to the B-chain coding region, may conveniently be obtained by conventional mutagenesis techniques to introduce the SstI site into a vector (c) encoding the u-PA polypeptide, conveniently at nucleotide position 563. The u-PA polypeptide is conveniently held between the HindIII and BglII sites of a suitable vector, such as pTRE12 (EP-A-0 201 153).

The expression of the DNA polymer encoding the hybrid PA in a recombinant host cell may be carried out by means of a replicable expression vector capable, in the host cell, of expressing the DNA polymer. The expression vector is novel and also forms part of the invention.

The replicable expression vector may be prepared in accordance with the invention, by cleaving a vector compatible with the host cell to provide a linear DNA segment having an intact replicon, and combining said linear segment with one or more DNA molecules which, together with said linear segment, encode the hybrid PA, under ligating conditions.

The ligation of the linear segment and more than one DNA molecule may be carried out simultaneously or sequentially as desired.

Thus, the DNA polymer may be preformed or formed during the construction of the vector, as desired.

The choice of vector will be determined in part by the host cell, which may be prokaryotic, such as *E. Coli*, or eukaryotic, such as mouse C127, mouse myeloma, chinese hamster ovary or yeast. Suitable vectors include plasmids, bacteriophages, cosmids and recombinant viruses.

The preparation of the replicable expression vector

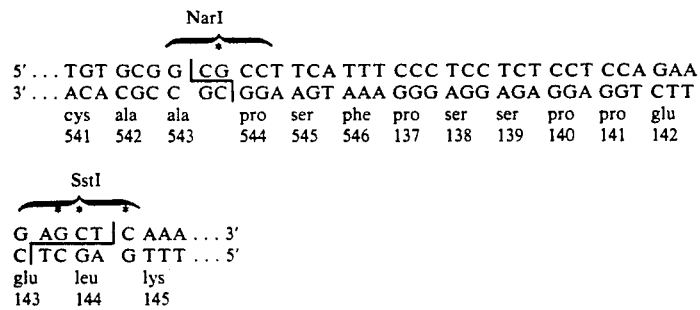

Amino acids marked 541–546 are the C-terminal residues of a peptide sequence comprising residues 1 to 546 of plasminogen. Amino acids marked 137–145 are the may be carried out conventionally with appropriate enzymes for restriction, polymerisation and ligation of the DNA, by procedures described in, for example, Maniatis et al., cited above. Polymerisation and ligation may be performed as described above for the preparation of the DNA polymer. Digestion with restriction enzymes may be performed in an appropriate buffer at a temperature of 20°-70° C., generally in a volume of 50 μl or less with 0.1-10 μg DNA.

The recombinant host cell is prepared, in accordance with the invention, by transforming a host cell with a replicable expression vector of the invention under transforming conditions. Suitable transforming conditions are conventional and are described in, for example, Maniatis et al., cited above, or "DNA Cloning" Vol. II, D. M. Glover ed., IRL Press Ltd, 1985.

The choice of transforming conditions is determined by the host cell. Thus, a bacterial host such as E. coli may be treated with a solution of $CaCl_2$ (Cohen et al, Proc. Nat. Acad. Sci., 1973, 69, 2110) or with a solution comprising a mixture of RbCl, $MnCl_2$, potassium acetate and glycerol, and then with 3-[N-morpholino]-propane-sulphonic acid, RbCl and glycerol. Mammalian cells in culture may be transformed by calcium co-precipitation of the vector DNA onto the cells.

The invention also extends to a host cell transformed with a replicable expression vector of the invention.

Culturing the transformed host cell under conditions permitting expression of the DNA polymer is carried out conventionally, as described in, for example, Maniatis et al and "DNA Cloning" cited above. Thus, preferably the cell is supplied with nutrient and cultured at a temperature below 45° C.

The hybrid PA expression product is recovered by conventional methods according to the host cell. Thus, where the host cell is bacterial, such as E. coli it may be lysed physically, chemically or enzymatically and the protein product isolated from the resulting lysate. Where the host cell is mammalian, the product may generally be isolated from the nutrient medium.

The DNA polymer may be assembled into vectors designed for isolation of stable transformed mammalian cell lines expressing the hybrid PA; e.g. bovine papillomavirus vectors or amplified vectors in chinese hamster ovary cells (DNA cloning vol. II D. M. Glover ed. IRL Press 1985; Kaufman, R. J. et al., Molecular and Cellular Biology 5, 1750-1759, 1985; Pavlakis G. N. and Hamer, D. H., Proceedings of the National Academy of Sciences (USA) 80, 397-401, 1983; Goeddel, D. V. et al., European Patent Application No. 0093619, 1983).

It will be appreciated that, depending upon the host cell, the hybrid PA prepared in accordance with the invention may be glycosylated to varying degrees. Furthermore, as observed by Pohl et. al., Biochemistry, 1984, 23, 3701-3707, varying degress of glycosylation may also be found in unmodified, naturally occurring t-PA. Plasminogen also exhibits varying degrees of glycosylation (Hayes M. L, J. Biol. Chem. 254: 8768, 1979). Mutant forms of the hybrid PA are also contemplated in which glycosylation sites are removed by genetic engineering techniques, for example as taught in EP-A-0238304, EP-A-0225286, DE-3537176, WO 87/04722 or EP-0236289. The hybrid PA of the invention is understood to include such glycosylated variations.

It will also be appreciated that, depending upon the expression conditions, the hybrid PA prepared in accordance with the invention may exist in the single or two chain forms or mixtures thereof. The invention extends to all such forms.

The hybrid PA of the invention comprises the B-chain of native t-PA or u-PA linked to an A-chain comprising the five kringle domains derived from plasminogen and linking sequence of amino acids comprising residues 264 and 275 of t-PA or residues 158 and 148 of u-PA.

This hybrid PA A-chain may be employed as one chain of a fibrinolytically active hybrid protein such as disclosed in EP-0 155 387. The hybrid A-chain, DNA encoding the hybrid A-chain and a hybrid protein comprising the hybrid A-chain linked to the B-chain of a fibrinolytically active protease, the catalytic site of which is optionally blocked by a removable blocking group, all form part of the invention.

The hybrid A-chain may be prepared by separation from the B-chain thereof by mild reduction. Alternatively the hybrid A-chain may be prepared by expressing DNA coding therefor in a recombinant host cell and recovering the hybrid A-chain product. The hybrid protein comprising the hybrid A-chain linked to the B-chain of a fibrinolytically active protease may be prepared by (a) mixing said A- and B-chains under oxidative conditions; or (b) ligating DNA encoding said A-chain to DNA encoding said B-chain and expressing the ligated DNA in a prokaryote or eukaryote host; and thereafter optionally blocking the catalytic site of the hybrid protein with a removable blocking group. The oxidation and reduction conditions are as generally described in EP-A-0 155 387.

The resulting hybrid protein may be used in any of the methods and compositions described hereinafter for the hybrid PA itself.

The hybrid PA of the invention or conjugate thereof can be further derivatised such that any catalytic site essential for fibrinolytic activity is optionally blocked by a removable blocking group.

As used herein the expression 'removable blocking group' includes groups which are removable by hydrolysis at a rate such that the pseudo-first order rate constant for hydrolysis is in the range of $10^{-6}$ sec$^{-1}$ to $10^{-2}$ sec$^{-1}$, more preferably $10^{-6}$ sec$^{-1}$ to $10^{-3}$ sec$^{-1}$, in isotonic aqueous media at pH 7.4 at 37° C.

Such blocking groups are described in European Patent No. 0009879 and include acyl groups such as optionally substituted benzoyl or optionally substituted acryloyl.

Suitable optional substituents for benzoyl blocking groups include halogen, $C_{1-6}$ alkyl, $C_{1-6}$ alkoxy, $C_{1-6}$ alkanoyloxy, $C_{1-6}$ alkanoylamino, amino or p-guanidino.

Suitable optional substituents for acryloyl blocking groups include $C_{1-6}$ alkyl, furyl, phenyl or $C_{1-6}$ alkylphenyl. In a preferred aspect, the removable blocking group is a 2-aminobenzoyl group substituted in the 3- or 4-position with a halogen atom and optionally further substituted with one or more weakly electron-withdrawing or electon-donating groups, wherein the pseudo first order rate constant for hydrolysis of the derivative is in the range $6.0 \times 10^{-5}$ to $4.0 \times 10^{-4}$ sec$^{-1}$ when measured in a buffer system consisting of 0.05M sodium phosphate, 0.1M sodium chloride, 0.01% v/v detergent comprising polyoxyethylenesorbitan monoleate having a molecular weight of approximately 1300, at pH 7.4 at 37° C.

Preferably the pseudo first order rate constant for hydrolysis of the derivative is in the range $6.0 \times 10^{-5}$ to $2.75 \times 10^{-4}$ s$^{-1}$, preferably $6.0 \times 10^{-5}$ to $2.5 \times 10^{-4}$ s$^{-1}$, more preferably $6.0 \times 10^{-5}$ to $2.0 \times 10^{-4}$ s$^{-1}$, still more preferably $6.0 \times 10^{-5}$ to $1.5 \times 10^{-4}$ s$^{-1}$ and most preferably $7.0 \times 10^{-5}$ to $1.5 \times 10^{-4}$ s$^{-1}$.

Preferably, the 2-aminobenzoyl group is substituted with a halogen atom in the 4-position.

Preferably, the halogen atom is fluorine, chlorine or bromine.

When the group is further substituted, preferred groups include $C_{1-6}$ alkyl, $C_{1-6}$ alkoxy and $C_{1-6}$ alkenyl substituents in the 3- or 5-positions of the ring.

Preferably, the blocking group is 4-fluoro-2-aminobenzoyl, 4-chloro-2-aminobenzoyl or 4-bromo-2-aminobenzoyl.

The abovementioned substituted 2-aminobenzoyl blocking groups may be used to derivatise any plasminogen activator comprising the serine protease domain of t-PA or u-PA. This novel group of blocked enzymes within the broad scope of EP-0009879 but not specifically disclosed therein have been found to undergo regeneration of functional active centres at rates corresponding to pseudo first-order rate constants of $6 \times 10^{-5}$ to $4 \times 10^{-4}$ $sec^{-1}$. The latter range of rate constants is especially appropriate for the provision of fibrinolytic activity during the treatment by thrombolytic agents of acute myocardial infarction.

Accordingly, in a further aspect, the invention provides a derivative of a plasminogen activator comprising the serine protease domain of t-PA or u-PA, in which the catalytic site essential for plasminogen activator activity is blocked by a 2-aminobenzoyl group substituted in the 3- or 4-position with a halogen atom and optionally further substituted with one or more weakly electron-withdrawing or electon-donating groups, wherein the pseudo first order rate constant for hydrolysis of the derivative is in the range $6.0 \times 10^{-5}$ to $4.0 \times 10^{-4}$ $sec^{-1}$ when measured in a buffer system consisting of 0.05M sodium phosphate, 0.1M sodium chloride, 0.01% v/v detergent comprising polyoxyethylenesorbitan monoleate having a molecular weight of approximately 1300, at pH 7.4 at 37° C.

A suitable detergent for use in the buffer is the product having the tradename Tween 80.

Suitable examples of the blocking group are as described above.

The term plasminogen activator includes human tissue plasminogen activator (t-PA) and urokinase (both high and low molecular weight forms). Such enzymes are obtained from mammalian blood, urine or tissues or by recombinant DNA methods where heterologous host organisms such as bacteria, yeasts, fungi or mammalian cells express genes specifying the enzymes. The term also includes:

(a) fibrinolytically active hybrid proteins disclosed in EP-A-0155387, such as $lys_{78}$ plasmin A-chain-/$ile_{276}$ t-PA;

(b) protein conjugates disclosed in EP-A-0152736, such as urokinase linked to reversibly blocked plasmin;

(c) derivatives of fibrinolytic enzymes disclosed in EP-A-0155388 in which the human protein component comprises the serine protease domain of t-PA or urokinase, such as urokinase reversibly linked to the active centre of human plasmin;

(d) conjugates comprising a fibrinolytic enzyme linked to a water-soluble polymer by means of a reversible linking group as disclosed in EP-A-0183503; and (e) genetically engineered derivatives including muteins of naturally occurring plasminogen activators such as those disclosed in EP-A-0201153, EP-A-0107589, WO-8604351, EP-0041766, EP-0213794, EP-0199574, EP-A-0240334, EP-A-0241208, EP-A-0241209, EP-A-0241210, EP-A-0233013, European Patent Application No. 88301897.0 and U.S. Ser. No. 163959/ European Patent Application No. 88304626.0, EP-A-0213794, EP-A-0231883, WO 8704722, EP-A-0242836, EP-A-0234051, EP-A-0253582, EP-A-0253241, WO-8604351, EP-A-0236040, EP-A-0200451, EP-A-0238304, EP-A-0225286, DE-3537176, EP-A-0236289, WO-8601538, EP-0227462, AU-8661804, WO-8703906 and EP-0199574, such as des($cys_{51}$-$asp_{87}$)t-PA;

provided that the enzymes listed in (a) to (e) comprise the serine protease domain of t-PA or urokinase.

Preferred derivatives of this invention include the following:

4-fluoro-2-aminobenzoyl urokinase, 4-chloro-2-aminobenzoyl urokinase or t-PA, and 4-bromo-2-aminobenzoyl t-PA;

2-amino-4-chlorobenzoyl($lys_{78}$ plasmin A-chain)$ile_{276}$ t-PA;

the 4-chloro- and 4-fluoro-2-aminobenzoyl derivatives of the conjugates in which urokinase (high or low molecular weight) is linked reversibly to the active centre of human plasmin;

the 4-chloro-2-aminobenzoyl derivative of des($cys_{51}$-$asp_{87}$)t-PA; and, most preferably, 4-chloro-2-aminobenzoyl plg 1–544/t-PA 262–527 (two chain) including the $glu_1$ and $lys_{78}$ variants and mixtures thereof, and 4-chloro-2-aminobenzoyl plg 1–541/t-PA 262–527 (two chain) including the $glu_1$ and $lys_{78}$ variants and mixtures thereof.

The present invention also provides a process for preparing a derivative of the invention, which process comprises reacting the plasminogen activator with a blocking agent JK in which i is a locating group which mediates binding of the agent to the catalytic site of the enzyme and K is a 2-aminobenzoyl group substituted in the 3- or 4-position with a halogen atom and optionally further substituted with one or more weakly electron-withdrawing or electron-donating groups.

Examples of group i include 4-amidinophenyl and 2-chloro-4-amidinophenyl.

Preferred agents JK are 4-amidinophenyl 2'-amino-4'-fluorobenzoate; 4-amidinophenyl 2'-amino-4'-chlorobenzoate and 4-amidinophenyl 2'-amino-4'-bromobenzoate.

Blocking agents JK as above defined are novel and form part of the invention.

The blocking reactions are preferably carried out in aqueous media, at a pH in the range 7.0 to 8.5 and at temperatures in the range 0° C. to 30° C. The preferred concentration range for the blocking agent is 0.01 to 2.0 millimolar, and the preferred enzyme concentration range is 1 to 500 micromolar.

In certain cases, particularly with plasminogen activators such as t-PA and those structurally related to or derived from plasminogen, it is desirable to carry out the blocking reaction in the presence of enzyme solubilising or stabilising additives such as 1-arginine, 1-lysine or 6-aminohexanoic acid. The materials have been found to be compatible with the blocking agents of the invention.

The blocking agents JK may be prepared by the reaction of the appropriate substituted benzoic acid with the appropriate alcohol in an organic base such as pyridine and in the presence of a condensing agent such as dicyclohexylcarbodiimide. The condensation reaction may be performed without prior protection of the 2-amino substituent in the acid component.

The precursor substituted anthranilic acids may be prepared by a variety of methods known in the art. In general, the relative positions of the desired substituents will determine the chosen starting material. Where an optional substituent such as methyl or methoxy is required, this is generally present in the starting material. The halo, amino and carboxylic acid groups are successively introduced, as necessary, in any appropriate order, by conventional aromatic substitution. Amino and carboxylic acid groups may be provided in precursor form. Amino groups may be obtained from nitro groups by reduction. Carboxylic acid groups may be obtained from methyl groups by oxidation or from ester or thioester groups by hydrolysis. During successive introduction of substituents, it may be necessary to protect amino and/or carboxylic acid groups.

One preferred route comprises the preparation of an appropriate aminotoluene derivative by reduction of the corresponding nitrotoluene, protection of the amino group (for example by acetylation), oxidation of the methyl function to a carboxylic acid group (for example with potassium permanganate) and removal of the protecting group by hydrolysis.

4-Halo-5-methyl anthranilic acids may be prepared by firstly protecting the carboxylate in 4-amino-m-toluic acid with thionyl chloride dimethylamine (to give the dimethylamide), then nitrating the ring at the 2-position with excess butyl lithium/acetyl nitrate, diazotising the free amino group and substituting a halogen atom using the Sandmeyer reaction, reducing the nitro group to give the amine in the 2-position and finally hydrolysing the dimethylamide to the free acid. The same compounds (or, for example, the corresponding 5-methoxy derivatives) may also be prepared from 4-nitro toluene or 4-nitro anisole by halogenation at the 2-position with chlorine/aluminium chloride, reduction to the amine which is then protected by acetylation, insertion of a carboxyl precursor by electrophilic substitution with aluminium chloride and chloroformate ester or thioester and finally hydrolysis of both acetyl and ester/thioester groups to liberate the unprotected amine and carboxyl functions.

The hybrid PA and derivatives of the invention are suitably administered in the form of a pharmaceutical composition.

Accordingly the present invention also provides a pharmaceutical composition comprising a hybrid PA or derivative of the invention in combination with a pharmaceutically acceptable carrier.

The compositions according to the invention may be formulated in accordance with routine procedures as pharmaceutical compositions adapted for intravenous administration to human beings.

Typically compositions for intravenous administration are solutions of the sterile enzyme in sterile isotonic aqueous buffer. Where necessary the composition may also include a solubilising agent to keep the hybrid PA or derivative in solution and a local anaesthetic such as lignocaine to ease pain at the site of injection. Generally, the hybrid PA or derivative will be supplied in unit dosage form for example as a dry powder or water free concentrate in a hermetically sealed container such as an ampoule or sachette indicating the quantity of protein in activity units. Where composition comprises a derivative of the invention or where the hybrid PA includes a removable blocking group, an indication of the time within which the free protein will be liberated may be given. Where the protein is to be administered by infusion, it will be dispensed with an infusion bottle containing sterile pharmaceutical grade 'Water for Injection' or saline. Where the protein is to be administered by injection, it is dispensed with an ampoule of sterile water for injection or saline. The injectable or infusable composition will be made up by mixing the ingredients prior to administration.

The quantity of material administered will depend upon the amount of fibrinolysis required and the speed with which it is required, the seriousness of the thromboembolic condition and position and size of the clot. The precise dose to be employed and mode of administration must per force in view of the nature of the complaint be decided according to the circumstances by the physician supervising treatment. However, in general, a patient being treated for a thrombus will generally receive a daily dose of from 0.01 to 10 mg/kg of body weight, such as 0.10 to 2.0 mg/kg, either by injection in for example up to five doses or by infusion.

Within the above indicated dosage range, no adverse toxicological effects are indicated with the compounds of the invention.

Accordingly, in a further aspect of the invention there is provided a method of treating thrombotic diseases, which comprises administering to the sufferer an effective non-toxic amount of hybrid PA of the is invention.

In another aspect the invention provides the use of a hybrid PA of the invention for the manufacture of a medicament for the treatment of thrombotic diseases.

The invention also provides a hybrid PA of the invention for use as an active therapeutic substance and in particular for use in the treatment of thrombotic diseases.

The present invention further provides a method of treatment of thromboembolic diseases, in particular acute myocardial infarction, which method comprises administering to the sufferer an effective, non-toxic amount of a derivative of the invention.

The invention also provides the use of a derivative of the invention for the manufacture of a medicament for the treatment of thromboembolic diseases, in particular acute myocardial infarction.

In a further aspect, the invention provides a derivative of the invention for use as an active therapeutic substance, in particular for the treatment of thromboembolic diseases such as acute myocardial infarction.

The following Methods and Examples illustrate the invention.

I. General Methods used in Examples (i) DNA cleavage

In general the cleavage of about 1 μg of plasmid DNA or DNA fragments was effected using about 5 units of a restriction enzyme (or enzymes) in about 20 μl of an appropriate buffer solution.

(ii) Generation of blunt ends: If blunt ends were required they were produced by treating the DNA preparation with DNA Polymerase I, Klenow fragment as described by Maniatis et al, (Molecular Cloning-A Laboratory Manual, Cold Spring Harbor Laboratory, 1982), or alternatively (where indicated) by digestion using Mung Bean nuclease (Molecular Cloning-A Laboratory Manual, Cold Spring Harbor Laboratory, 1982).

(iii) Generation of 'Sticky ends' using linkers: Short kinased oligonucleotide linkers encoding single or multiple restriction sites were ligated onto blunt ended fragments, the linker(s) was digested with the appropriate restriction endonuclease producing the required 'sticky end' necessary for further manipulation. (Molecular Cloning-A Laboratory Manual, Cold Spring Harbor Laboratory, 1982)

(iv) Ligation of DNA Fragments: Ligation reactions were carried out as described in Maniatis et al, (Molecular Cloning—A Laboratory Manual, Cold Spring Harbor Laboratory, 1982).

(v) Transformation of plasmid DNA into E.coli HB101 or E.coli DH5α cells used competent HB101 or DH5a cells supplied by Gibco BRL (Paisley, Scotland), according to the manufacturers instructions.

(Vi) Plasmod preparation: Large scale preparation of plasmid DNA and plasmid mini-preparations were carried out as described in Maniatis et al, (Molecular Cloning —A Laboratory Manual, Cold Spring Harbor Laboratory, (1982)).

(vii) Isolation of DNA fragments from low-melting-point (LMP) agarose gels: DNA fragments were isolated from LMP agarose gels as described by Maniatis et al, (Molecular Cloning-A Laboratory Manual, Cold Spring Harbor Laboratory, 1982). Alternatively f the excised gel band was purified using GENE-CLEAN TM, (Stratech Scientific, London) used according to the manufacturers instructions.

(viii) Oligonucleotides: oligonucleotides were made on Applied Biosystems 381A DNA Synthesizer according to the manufacturers instructions and were kinased as described in Maniatis et al, op. cit. When used in plasmid construction the oligonucleotides were annealed by heating together at 95° C. for 5 minutes and cooling slowly to room temperature. The annealed oligonucleotides were then ready for ligation. If four oligonucleotides were to be annealed the annealing reaction was followed as described above but was carried out as 2 reactions each containing a pair of complementary oligonucleotides. After cooling the 2 reactions were mixed prior to ligation.

(ix) DNA secruencing
(a) Single-strand method

Nucleotide sequence determination was carried out by the Sanger dideoxy chain termination method as described in Sanger, S., Nicklen, S. and Coulson, A. R. (1977) Proc. Natl. Acad. Sci. USA 74, 5463-5467 using $^{35}$S-labelled DATP.

(b) Double-strand method

Sequencing was carried out using Sequenase TM (United States Biochemical Corporation) essentially according to the manufacturers instructions.

(x) Transient expression plasminogen activators from HeLa cells
(a) Small-scale

Cell preparation: cells were trypsinised and plated out at approx. $2.4 \times 10^5$ cells per 35 mm dish and incubated in 1.5 ml growth medium (this is Hepes buffered RPM1 1640 medium (041-2400) containing 10% Serum (021-6010), stock solution of penicillin/streptomycin (043-5070), 2% sodium bicarbonate solution (043-5080), 1% stock Glutamine (043-5030); Gibco, Parsley, Scotland) at 37° C. in a humidified incubator in an atmosphere of 5% $CO_2$/95% air. After 72 h the cells were refed, and used for transfection 24 h later.

Transfection procedure: cultures were changed to Eagles MEM (041-1095), 10% serum, 1% penicillin/-streptomycin, 1% Glutamine and 1% non-essential amino acids (043-1140) 3 h before transfection. The transfections used calcium coprecipitation as described in 'DNA Cloning' Ed. D. M. Glover (Chap. 15, C. Gorman). Glycerol shock and 5 mM butyrate treatments were used. Plasminogen activator(s) secreted by transfected cells was harvested in 1.0 ml RPMI 1640 medium (as above but serum-free, containing 4% soybean peptone (Sigma)) for 24 h and activity was measured using fibrin plates with reference to normal t-PA (J. H. Robinson, Thromb. Res., 1984; 33, 155).

Alternatively the HeLa cells were plated at $5 \times 10^5$ per dish, in which case the cells were refed after only 24 h and then used as above.

(b) Large-scale

Cell preparation: cells were trypsinised and plated out at a density of approx. $2.5 \times 10^6$ cells per 175cm$^2$ flask in 30 ml growth medium (above). After 72 h an extra 25 ml of growth medium was added and the cells were used for DNA transfection 24 h later (as above). 25 ml of harvest medium were used per flask.

Alternatively the cells were plated at a density of approximately $2.0 \times 10^6$ cells per flask and 25 ml of growth medium were added after 96 h incubation and the cells used as above.

The two seeding rates and feed times used in the small and large-scale protocols were designed to allow convenient timing of experiments. Both sets of protocols allowed efficient expression of activator(s).

(xi) Western blotting/Immunogold silver staining

Following SDS PAGE, proteins were blotted onto nitrocellulose (NC) by electrophoretic transfer overnight at 4° C.,40V, 100 mA in 25 mm Tris/192 mM Glycine/20% (v/v) Methanol pH 8.3. Unreacted sites on the NC were blocked with 5% bovine serum albumin (BSA)/phosphate-buffered saline (PBS) pH 7.2 for 1 h, followed by a 2 h incubation with rabbit anti-t-PA B chain IgG (48µg/ml) in 1% BSA/0.5% Tween 80/PBS pH 7.2 (diluent). The NC was washed, $3 \times 5$ mins, in 0.5% Tween 80/PBS pH 7.2 and then incubated for 1 h in biotinylated secondary antibody (Janssen; 2 µg/ml in diluent). The NC was washed as above and incubated in Auroprobe TM BL plus streptavidin (Janssen) 1:100 in diluent for 2 h. The NC was washed as above, followed by $1 \times 1$ min in deionised water, and silver enhanced using IntenSE TM II kit (Janssen) for 15-20 min. All steps were carried out at ambient temperature with gentle shaking.

II. Identification of nucleotides, amino acid residues, N-termini, protein domains and chain nature in the examples (i) Sequences All t-PA numbering as in Pennica et al (1983) op. cit.; plasminogen amino acid numbering based on Sottrup-Jensen et al (1978) Atlas of Protein Sequence and Structure Vol. 5, Suppl. 3, p91, National Biomedical Research Foundation, Silver Spring, MD., but updated to include the extra amino acid residue identified by Forsgren, M. et al (1987) FEBS Letters, 213, 254-260. Plasminogen nucleotide sequences as in Forsgren et al. (op.cit.). All urokinase numbering corresponds to Holmes et al., (1985) Bio Technology 3, 923-929.

(ii) N-termini
1. t-PA

The mature N-terminus is normally believed to be equivalent to ser$_1$ (Pennica et al., 1983). Other forms also exist e.g. $gly_{-3}$ or $val_{+4}$ (Pohl et al., 1986 FEBS letters, 168 29-32).

2. plasminogen $glu_1$ indicates the protein is believed to comprise the native (nascent) plasminogen N terminus i.e. amino acid residues 1 onwards.

$lys_{78}$ indicates the protein is believed to comprise the processed $lys_{78}$ N terminus. Alternative processed N-termini e.g. $met_{69}$ and $val_{79}$ are known in nature (Miyashita et al., 1988).

(iii) Protein Domains

The protein domains described in the examples have been abbreviated for convenience and are defined as follows:

| 1. t-Pa: | |
|---|---|
| $F^l$ = amino acid residues | 6 to 43 inclusive |
| $G^l$ = amino acid residues | 51 to 84 inclusive |
| $B^l$ = amino acid residues | 276 to 527 inclusive |
| 2. plasminogen: | |
| $K_1^p$ = amino acid residues | 84 to 162 inclusive |
| $K_2^p$ = amino acid residues | 166 to 243 inclusive |
| $K_3^p$ = amino acid residues | 256 to 333 inclusive |
| $K_4^p$ = amino acid residues | 358 to 435 inclusive |
| $K_5^p$ = amino acid residues | 462 to 541 inclusive |
| the 5 plasminogen kringles $K_1$-$K_5$ = amino acid residues | 84 to 541 inclusive |

(iv) Chain nature sc, indicates that the protein is in single chain form.
tc, indicates that the protein is in two chain form.

(v) Vectors pTRE12—(EP-0201153)—basic expression vector
pTRE15—(EP-0201153)—encodes wild-type t-PA
pTRE24—(EP-0207589)—encodes des($cys_{51}$-$asp_{87}$)t-PA
pTR6F—(EP-0241208)—encodes t-PA finger domain III. Construction and expression of hybrid proteins The expression of the proteins of Examples 1 to 7 is carried out in Hela cells

EXAMPLE 1

Plasminogen 1-544/t-PA 262-527 04

1.1 Construction of a plasmid carrying plasminogen cDNA

A plasminogen cDNA clone was obtained from a human liver cDNA library after screening with an oligonucleotide probe of sequence (A):

5'CC CCT CAC ACA CAT AAC AGG 3' (A)

corresponding to nucleotides 49 to 68 of the sequence described in Malinowski et al Biochemistry 23, p4243 (1984).

The DNA sequence of the portion of the plasminogen cDNA clone coding for the A chain of the protein was determined and two differences to the plasminogen cDNA sequence of Forsgren et al (1987) were noted.

The nucleotide at position 846 is T, the nucleotide at position 948 is G.

The 5' end of the clone was shown to correspond to nucleotide 27 of the sequence of Forsgren et al (1987).

Plasminogen cDNA was subcloned into the vector PUCS (Vieira and messing, 1982, Gene 19, 259) between the HincII and EcoRI sites to create plasmid pTRH6 FIG. 1a.

1.2 modification of PTRE12

The single NarI site formerly in plasmid pTRE12 (EP-A-0 201 153) was destroyed by restriction cutting, blunt ending and religation forming pTRE12D Nar. Removal of the NarI site aided further manipulation.

1.3 construction of a hybrid plasminogen: t-PA cDNA molecule (plasmid pTRH204)

(All plasminogen nucleotide numbering corresponds to Forsgren et al., 1987, op.cit.)

Three fragments were prepared by restriction digestion and agarose gel electrophoresis. These fragments are as follows:

I: approximately 1.6 kb: from HindIII plus AhaII digest (HindIII [5' to the plasminogen coding sequence] to AhaII(1572)) of pTRH6.

II: approximately 0.18 kb: from an AhaII plus DdeI digest (AhaII (1572) to DdeI (1748)) of pTRH6.

III: approximately 5.3 kb: largest fragment from a HindIII plus BglII digest, of pTRE12D Nar. This fragment carries pTRE12D Nar vector functions.

These fragments (I, II, III) were ligated with a kinased oligonucleotide linker (linker IV) comprising two oligonucleotides of sequence:

5' TCAGTGTGCGGCGCCTGGTACCA 3'  (B)

5' GATCTGGTACCAGGCGCCGCACAC 3'  (C)

After transformation into E.coli HB101 the plasmid pTRH9 (FIG. 2) was isolated.

The DNA in plasmid pTRH9 encodes most of the plasminogen-A chain, up to and including proline 544 i.e. kringles 1 to 5; the DNA encoding the plasminogen B-chain and the remainder of the A-chain were absent. Use of linker Iv in construction of pTRH9 introduces a unique NarI site, as may be seen from Table 1 (which shows the junction of fragments II and III and linker IV).

TABLE 1

Junction of fragments II and III and linker IV in plasmid pTRH9.

—Fragment II → ← ——— Linker IV ——— → ← — Fragment III—

```
         1745    DdeI      1755      NarI     1765      BglII
5' GAT GTC CC |T CA G TGT GCG G |CG* CCT GGT ACC A |GA TC  T 3'
3' CTA CAG GG  A GT|C ACA CGC C  GC| GGA CCA TGG T  CT AG|A 5'
    asp  val  pro  gln  cys  ala  ala  pro
    537  538  539  540  541  542  543  544
```

The plasminogen amino-acid sequence is shown
*This residue is C in plasminogen cDNA
Nucleotide numbering is included (above the sequence)

Plasmid pTRH9 was restricted with BglII and ligated with the 2kb BglII fragment encoding the mature t-PA polypeptide isolated from pTRE15 (EP-A-0 201 153).

Figure 3:
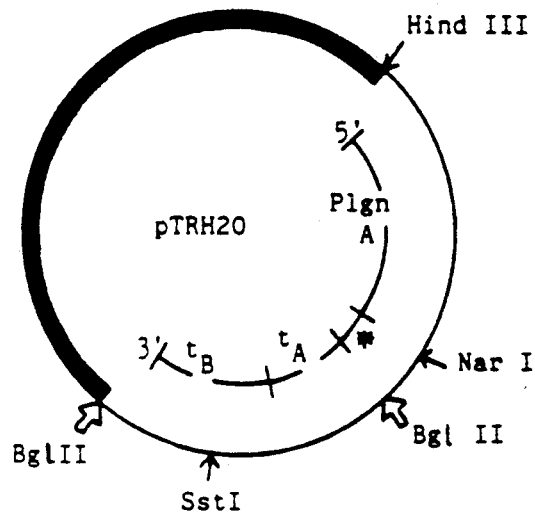

An *E.coli* HB101 clone carrying the t-PA insert in the same orientation (5'→3') as the plasminogen 'A' chain DNA was isolated; this plasmid was called pTRH20 (see FIG. 3).

Plasmid pTRH20 encodes a molecule comprising the five kringles of plasminogen (residues 1 to 544) linked to the N-terminus of mature t-PA via the tripeptide gly-thr-arg. The junction of the plasminogen A-chain DNA and t-PA A-chain DNA of plasmid pTRH20 is shown in Table 2.

TABLE 2

Junction of the plasminogen A-chain DNA and t-PA A chain DNA in plasmid pTRH20.

```
                                        BglII
5' CCT CAG TGT GCG GCG CCT GGT ACC A|GA TC T TAC CAA 3'
3' GGA GTC ACA CGC CGC GGA CCA TGG T CT AG|A ATG GTT 5'
   pro gln cys ala ala pro gly thr arg ser tyr gln
   539 540 541 542 543 544             1   2   3

<---------------------->  <------>  <-------->
      Plasminogen            linking     t-PA
       sequences            tripeptide  sequences
```

The DNA encoding the t-PA A-chain and part of the B-chain was removed from pTRH20 by restriction with NarI and SstI (located at t-PA nucleotide 1417 as described by Pennica et al 1983). The large SstI-NarI fragment (7.9 kb) was isolated (fragment V).

An approximately 0.4 kb BanII fragment (fragment VI) was isolated from pTRE15. The two relevant BanII sites are located at nucletotides 1024 and 1417 in the t-PA cDNA sequence described by Pennica et al (1983). BanII has a degenerate recognition site i.e.:

5'....G Pu GC Py C.....3'

3'....C Py CG Pu G.....5'

Note that the BanII site at 1417 is identical to the SstI site at 1417 and also that the sticky end created is compatible with an SstI sticky end. The 0.4 kb BanII fragment encodes most of t-PA B-chain.

Two oligonucleotides (D) and (E):

5'CGCCGTCGACCTGCGGCCTGAGACAG-
TACAGCCAGCCTCAGTTTCGCATC
AAAGGAGGGCT 3'                    (D)

5'CTCCTTTGATGCGAAACT-
GAGGCTGGCTGTACTGTCTCAGGCC-
GCAGGTC GACGG 3'                  (E)ps were synthesized, kinased and combined to form linker VII.

Linker VII has a 5' NarI sticky end, compatible with the NarI sticky end of fragment V and a 3' BanII sticky end compatible with the BanII (nucleotide 1024) sticky end of fragment VI.

Fragments V and VI together with linker VII were ligated and transformed into *E.coli* HB101. A plasmid (pTRH204) with the structure depicted in FIG. 4 was isolated.

The junction of fragment V and linker VII is shown in Table 3.

Joining of fragments V and VI via the BanII (1417) and SstI sticky ends completed the reconstruction of the t-PA B-chain coding region.

TABLE 3

Junction of fragment V and linker VII in plasmid pTRH204

```
... — Fragment V ———>  <——— linker VII ————————

DdeI              NarI
5' CCT CAG TGT GCG G|CG CCG TCG ACC TGC GGC CTG 3'
3' GGA GTC ACA CGC C GC|GGC AGC TGG ACG CCG GAC 5'
   pro gln cys ala ala pro ser* thr cys gly leu
   539 540 541 542 543 544      263 264 265 266

<--------------------|-------------------->
         plasminogen              t-PA
          sequences             sequences
```

The plasminogen and t-PA amino-acid sequences at the junction are shown (plasminogen numbering 539–544 and t-PA numbering 263–266). The serine residue denoted may be considered to be equivalent to plasminogen serine 545 or t-PA serine 262.

Plasmid pTRH204 was used to transfect human HeLa cells (as described in Methods) and produced a novel plasminogen activator (H204) believed to have the structure plasminogen 1-544/t-PA 262-527.

1.4 Alternative procedure for plasmid PTRH9

Figure 1B:
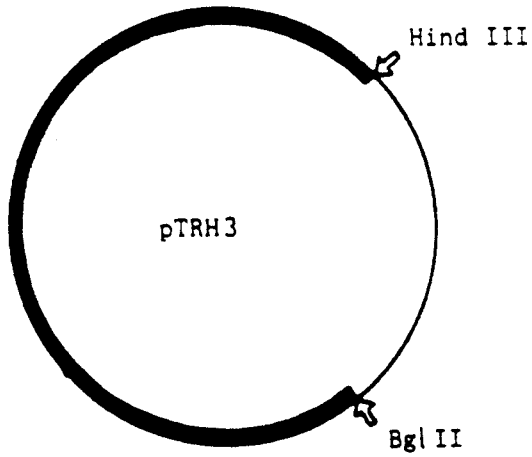

The plasminogen cDNA clone obtained from a human liver cDNA library after screening with oligonucleotide probe (A), is subcloned into the vector pTRE12 (EP-A-0 201 153) between the HindIII and BglII sites to create plasmid pTRH3 FIG. 1(b). The single NarI site formerly in plasmid pTRE12 is destroyed by restriction cutting, blunt ending and religation. Removal of the NarI site aids further manipulation.

Three fragments of pTRH3 are prepared by restriction digestion and agarose gel electrophoresis. These fragments are as follows:

I: approximately 1.6 kb: from a HindIII plus AhaII digest (HindIII [5' to the plasminogen coding sequence] to AhaII(1572)).

II: approximately 0.18 kb: from an AhaII plus DdeI digest (AhaII (1572) to DdeI (1748)).

III: approximately 5.3 kb: largest fragment from a HindIII plus BglII digest, carries the vector functions of pTRH3.

These fragments (I, II, III) are ligated with the kinased oligonucleotide linker Iv described above.

EXAMPLE 2

Plasminogen 1-544/t-PA 262-527(arg$_{275}$→gln)(H205)

Construction of plasmid pTRH205

A hybrid plasminogen activator molecule similar to that produced in Example 1 but differing only in the t-PA amino acid residue 275, which is glutamine in place of arginine, also forms part of this invention. The DNA coding for this plasminogen activator was prepared generally as described in Example 1, differing only in the nucleotide sequence of the linker in which the triplet coding for arg-275, CGC, in linker VII was replaced by CAG coding for gln-275. The resulting plasmid pTRH205 was used to transfect human HeLa cells (as described in Methods) and produced a novel plasminogen activator(H205) believed to have the structure plasminogen 1-544/t-PA 262-527 (arg$_{275}$→gln).

EXAMPLE 3

Plasminogen 1-541/t-PA 262-527(H37)

Construction of plasmid PTRH37

Plasmid pTRH37 was constructed by ligating 2 fragments from pTRH204 (Example 1) together with fragment VI from pTRE15 and an oligonucleotide linker (linker XI):

Fragment IX: 7.2kb fragment of pTRH204 from the SstI site in the t-PA B chain coding region (nucleotide 1417 in the t-PA sequence) to the BstXI site in the plasminogen A chain coding region (nucleotide 1209 in the plasminogen sequence) (Fragment IX thus contains all the vector sequences).

Fragment X: 484 bp fragment of pTRH204 from the BstXI site (1209) to the AvaII site in the plasminogen A chain coding region at nucleotide (1693).

Fragment VI: (SstI-BanII) has been described previously (Example 1).

Linker XI was formed by annealing 4 oligonucleotides (H,I,J and K) of sequences:

5'GTCCCTGGTG CTACACGACA
AATCCGCGGA AACTTTACGA
CTACTGTGAT GTCCCTCAGT
GTTCGACCTG CGGCC 3'    (H)

5'TGAGACAGTA CAGCCAGCCT
CAGTTTCGCA TCAAAGGAGG GCT 3'    (I)

5'CTCCTTTGAT GCGAAACTGA
GGCTGGCTGT ACTGTCTCAG
GCCGCAGGTC GAACACTGAGGG 3'    (J)

5'ACATCACAGT AGTCGTAAAG
TTTCCGCGGA TTTGTCGTGT
AGCACCAGG 3'    (K)

Figure 5:
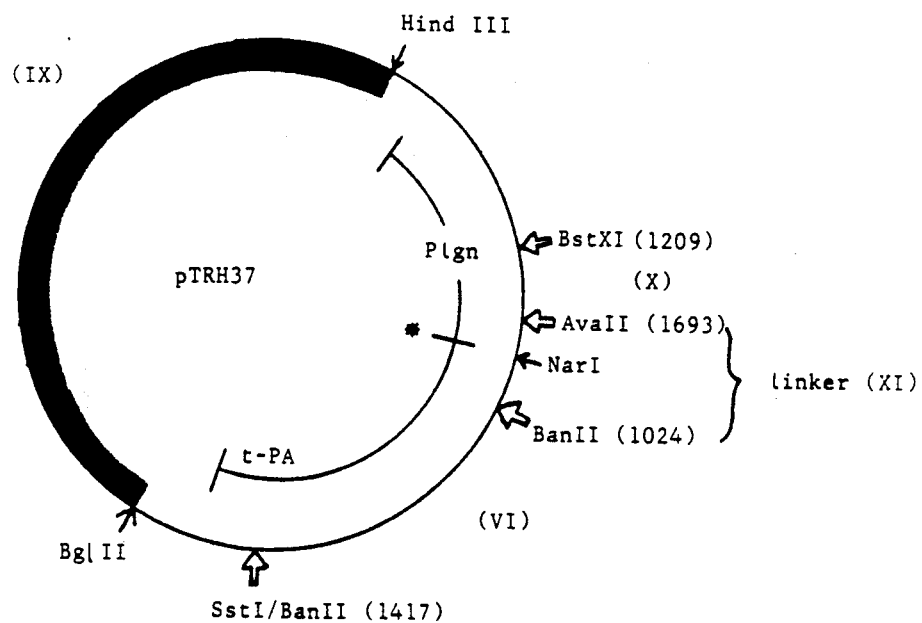

A plasmid (pTRH37) was isolated which has the structure shown in FIG. 5. The plasmid, when introduced into human HeLa cells, directed the expression of a novel plasminogen activator (H37) which has the same amino-acid sequence as protein H204 (Example 1) except for a deletion of the amino-acid residues alanine (542), alanine (543) and proline (544) immediately C-terminal to the Kringle 5 domain. The hybrid protein structure between Kringle 5 and the protease cleavage site is shown below using single letter notation:

541*                 276
$\underline{C}$STCGLRQYSQPQFR$\underline{I}$
                          t-PA B chain Residue 541 is the last cysteine in Kringle 5. The serine marked with an asterisk can be identified with serine$_{545}$ of plasminogen or serine$_{262}$ of t-PA.

EXAMPLE 4

Plasminogen 78-544/t-PA 262-527(HOO)

4.1 Construction of 'lys$_{78}$-cassette' plasmid

The lys$_{78}$-cassette plasmid is a form of the plasmid pTRE12 containing a piece of synthetic DNA that can be used to convert a plasminogen clone from the glu$_1$ form (glu$_1$ is the normal secreted N terminus) to the lys$_{78}$ form (lys$_{78}$ is then the N terminal amino acid).

A pair of kinased oligonucleotide linkers (R+S and T+V) comprising four oligonucleotides:

5'AGCTTCCAGT CCCAAAATGG
AACATAAGGA AGTGGTTCTT
CTACTTCTTT TATTTCTGAA
ATCGGGACAA GGAAAAGTGT ATCTCT
3'    (R)

5'ACACTTTTCC TTGTCCCGAT
TTCAGAAATA AAAGAAGTAG
AAGAACCACT TCCTTATGTT
CCATTTTGGG ACTGGA 3'    (S)

5'C AGAGTGCAAG ACTGGGAATG
GAAAGAACTA CAGAGGTACC
ATGTCCAAAA CAAAAAATGG
CATCACCTGT CAA 3'    (T)

5'GATCTTGACA GGTGATGCCA
TTTTTTGTTT TGGACATGGT
ACCTCTGTAG TTCTTTCCAT
TCCCAGTCTT GCACTCTGAG AGAT 3'    (V)

were prepared and ligated with the large HindIII-BglII fragment from pTRE12.

The resulting plasmid contained a region formed by the oligonucleotides comprising nucleotides 65-132 inclusive, joined to nucleotides 364-450 inclusive of native plasminogen. These nucleotides encode the signal sequence of 19 amino-acids as described by Forsgren et al, (1987) and amino acids 78-106 inclusive of the plasminogen A chain. A unique KpnI site was introduced (Table 4). The structure of the oligonucleotide insert was verified by DNA sequencing.

TABLE 4

Structure of the lys$_{78}$-cassette insert

```
                           met glu his lys glu val val leu leu
 AGCT  TCCAGTCCCAAA ATG GAA CAT AAG GAA GTG GTT CCT CTA
 Hind  AGGTCAGGGTTT TAC CTT GTA TTC CTT CAC CAA GAA GAT
 III leu leu leu phe leu lys ser gly gln gly* lys val tyr
 CTT CTT TTA TTT CTG AAA TCA GGT CAA GGA AAA GTG TAT
 GAA GAA AAT AAA GAC TTT AGT CCA GTT CCT TTT CAC ATA leu ser glu cys+ lys thr gly asn gly lys asn tyr arg
 CTC TCA GAG TGC AAG ACT GGG AAT GGA AAG AAC TAC AGA
 GAG AGT CTC ACG TTC TGA CCC TTA CCT TTC TTG ATG TCT gly thr met ser lys thr lys asn gly ile thr cys gln
 GGT ACC ATG TCC AAA ACA AAA AAT GGC ATC ACC TGT CAA  BglII
 CCA TGG TAC AGG TTT TGT TTT TTA CCG TAG TGG ACA GTT  CTAG
 KpnI                            SfaNI
```

The HindIII and BglII sticky ends were used to clone into the HindIII-BglII sites in pTRE12. SfaNl cuts at a site remote to its recognition sequence. gly* indicates the last residue of the signal sequence; cys+ is the first residue of the K$_1$P domain.

4.2 Construction of plasmid PTRH34 (Plasminogen 1-561/t-PA 276-527)

Plasmid pTRH34 was constructed essentially as described for plasmid pTRH204 (Example 1) by ligation of fragments v and VI together with a linker, but in place of linker VII, linker VIII was used. Linker VIII was formed by annealing 2 oligonucleotides (F and G):

```
5'CGCCTTCATT TGATTGTGGG
  AAGCCTCAAG TCGAGCCGAA
  GAAATGTCCC GGGAGGATCA
  AAGGAGGGCT 3'                                    (F)

5'CTCCTTTGAT CCTCCCGGGA
  CATTTCTTCG GCTCGACTTG
  AGGCTTCCCA CAATCAAATG AAGG 3'                    (G)
```

Figure 6:
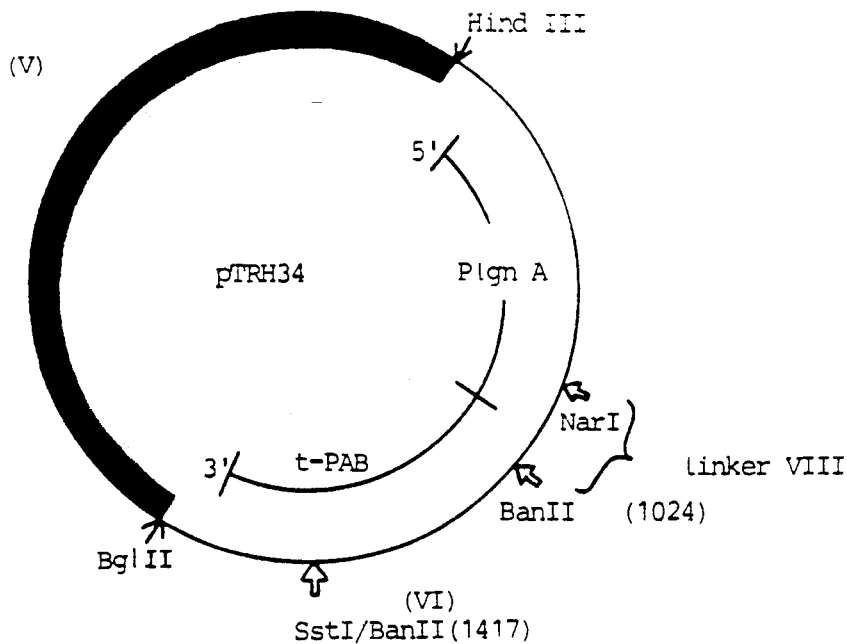

A plasmid pTRH34, with the structure shown in FIG. 6 was isolated. Plasmid pTRH34 when used to transfect human HeLa cells directs the synthesis of a novel plasminogen activator comprising the entire plasminogen A chain (glu$_1$-arg$_{561}$) linked directly to the complete t-PA B chain (ile$_{276}$-pro$_{527}$).

4.3 Construction of plasmid H00

Plasmid PTRH00 is a form of the plasmid pTRH204 (Example 1) in which the nucleotide sequence coding for amino acids glu$_1$-lys$_{77}$ of the plasminogen protein has been deleted.

The following DNA fragments were prepared by restriction endonuclease digestion and agarose gel electrophoresis:

Fragment I: approximately 160bp; from a HindIII plus SfaNl digest of the lys$_{78}$-cassette plasmid of Example 4.1 [i.e. from the HindIII site at the 5' end of the oligonucleotide linker sequence to the internal SfaNl site—see Table 4] and carries a nucleotide sequence coding for the signal sequence of 19 amino-acids as described by Forsgren et al (1987) joined to amino acids 78-104 inclusive (the SfaNl overhang extends to amino-acids 105 and 106) of the plasminogen A chain.

Fragment II: approximately 772 bp; from a SfaNl plus BstXI digest of pTRH34 of Example 4.2 (SfaNl(437) to BstXI(1209)), this carries most of K1P, all of K2P and K3P and the N-terminal section of K4P.

Fragment III: approximately 7Kb; from a BstXI and HindIII digest of pTRH204 (BstXI cuts at (1209) and HindIII is located 51 to the plasminogen coding sequence). This carries most of K4P, all of K5P, B' and the vector functions of pTRE12.

Figure 7:
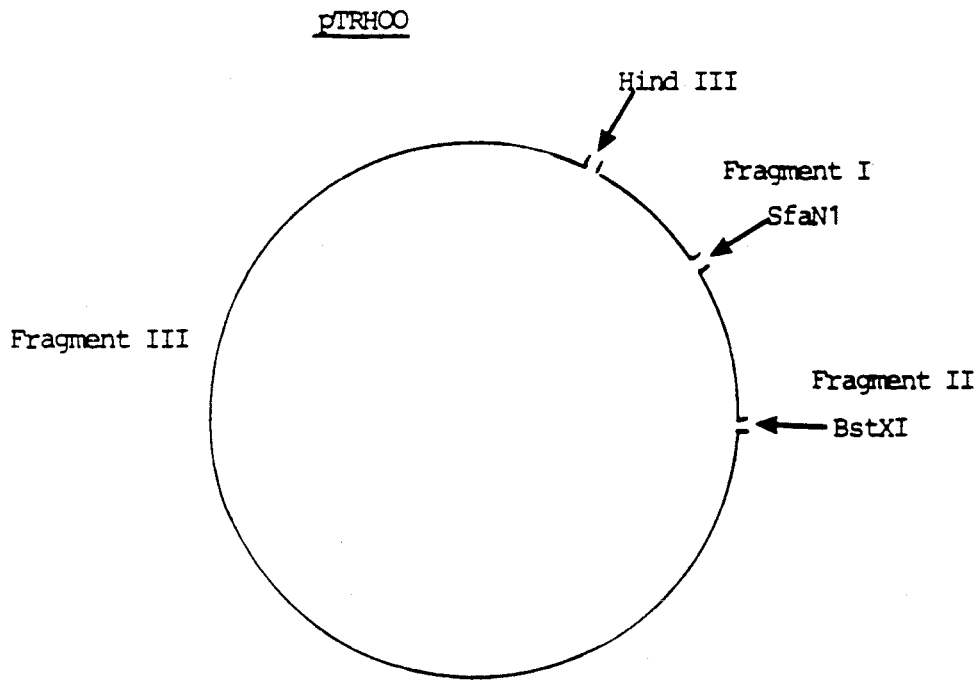

These fragments were ligated, after transformation into E.coli HB101 the plasmid PTRH00 was isolated (FIG. 7). PTRH00 was used to express the novel hybrid plasminogen activator H00 in HeLa cells.

EXAMPLE 5 t-PA 1-50/t-PA 88-91/pro-gly-ser/y)lasmin@en 84-544/t-PA 262-527 (H01)

Plasmid pTRH01 was designed to encode a mature protein in which the Ft coding domain from t-PA is joined to the 5' end of the K1P coding domain in plasmid PTRH00 (Example 4); the gross domain structure of the encoded native protein can be abbreviated as below:

F'K$_1$PK$_2$PK$_3$PK$_4$PK$_5$PB'

Construction of plasmid pTRH01

Two DNA fragments were prepared by restriction endonuclease digestion and agarose gel electrophoresis. These fragments were as follows:

Fragment I: approximately 36 obp: from a HindIII plus BamHI digest of plasmid pTR6F (disclosed in EP-0241208). The insert in pTR6F carries the 5' untranslated region and the signal/pro regions as well as the F' domain.

Fragment II: approximately 8kb: from a HindIII plus KpnI digest of plasmid PTRHOO (Example 4); this carries almost all of KlP, all of K2P, K3p, K4P, K5P, B' and the vector functions of pTRE12.

These fragments were ligated with a kinased oligonucleotide linker comprising two oligonucleotides (W and X) of sequence:

```
5'GATCTTGCAAGACTGGGAATG-
  GAAAGAACTACAGAGGTAC 3'                           (W)

5'CTCTGTAGTTCTTTCCATTCCCAGTCCT-
  GCAA 3'                                          (X)
```

After transformation into *E.coli* the plasmid pTRH01 (FIG. 8) was isolated. DNA sequencing confirmed the structure of the F'/K1P join (Table 5).

pTRH01 was used to express a novel hybrid plasminogen activator (H01), believed to have the sequence t-PA 1-50/t-PA88-91/pro-gly-ser/plasminogen 84-544/t-PA 262-527, in HeLa cells.

ate plasmid pTR6FG. PTR6FG also carries the 5' untranslated region and signal/pro regions.

6.2 Construction of pTRH02

Two DNA fragments were prepared by restriction endonuclease digestion and agarose gel electrophoresis. These fragments were as follows:

TABLE 5

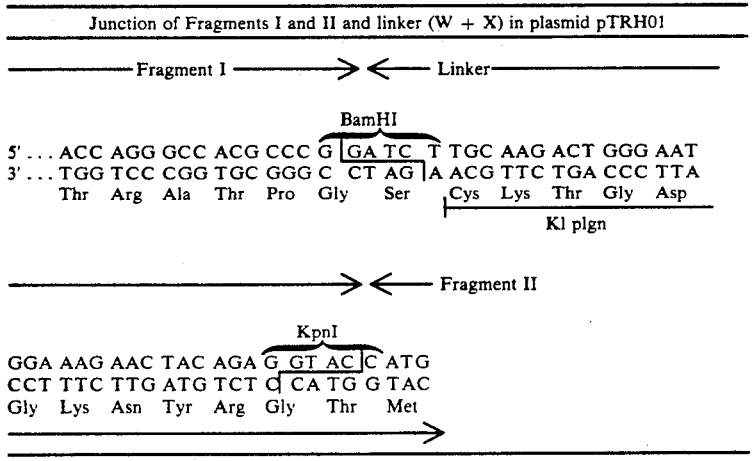

Junction of Fragments I and II and linker (W + X) in plasmid pTRH01

EXAMPLE 6 t-PA 1-91/pro-gly-ser/plasminogen 84-544/t-PA 262-527 (H02)

Plasmid pTRH02 was designed to encode a mature protein in which the F' and G' coding domains from t-PA are joined to the 5' end of the K1P coding domain in plasmid PTRH00 (Example 4); the gross domain structure of the encoded native protein can be abbreviated as below:

$$F'G'K_1PK_2PK_3PK_4PK_5PB'$$

6.1 Preparation of DNA encoding the t-PA finger and growth factor domains (plus the t-PA signal/pro and 5' untranslated regions)

6 μg of the plasmid pTRE15 (described in EP-A-0 201 153) was digested with MaeII. The MaeII cut DNA was flush-ended and kinased BamHI linkers (0.1 $A_{260}$ units; Amersham DC1203) of sequence 5'CCCGGATCCGGG3' were ligated to 5 μg of the flush-ended MaeII fragments. After ligation excess linkers were removed and cohesive 'sticky-ends' created by digestion with BamHI. The BamHI digest was electrophoresed on a 1% low melting point agarose gel. On this gel there was a group of three bands with mobility between that of the 1353 and 872 base pair fragments found in a lambda DNA-HindIII/ X174RF-HaeIII digest (Drigest TMIII, Pharmacia). The largest of these three bands, approximately 1200bp, was recovered (no special attempt was made to ensure that the other bands of similar mobility did not contaminate this preparation, since undesired molecules were eliminated in the cloning strategy). The 1200 bp fragment was digested with HindIII to create the desired approx. 47 obp fragment with a HindIII 5' sticky end and a 3' BamHI sticky end (converted from the MaeII site).

This finger-plus-growth-factor domain encoding DNA was sub-cloned into plasmid pTRE12 (EP-A-0207589) between the HindIII and BamHI sites to cre- Fragment I: approximately 47 obp: from a HindIII plus BamHI digest of plasmid pTR6FG.

Fragment II: approximately 8 kb: from a HindIII plus KpnI digest of plasmid PTRH00 (Example 5), carries almost all of K1P, all of K2P, K3P, K4P, K5P, B' and the vector functions of pTRE12.

These fragments were ligated with a kinased oligonucleotide linker comprising two oligonucleotides (w) and (X) of Example 5.

Figure 9:
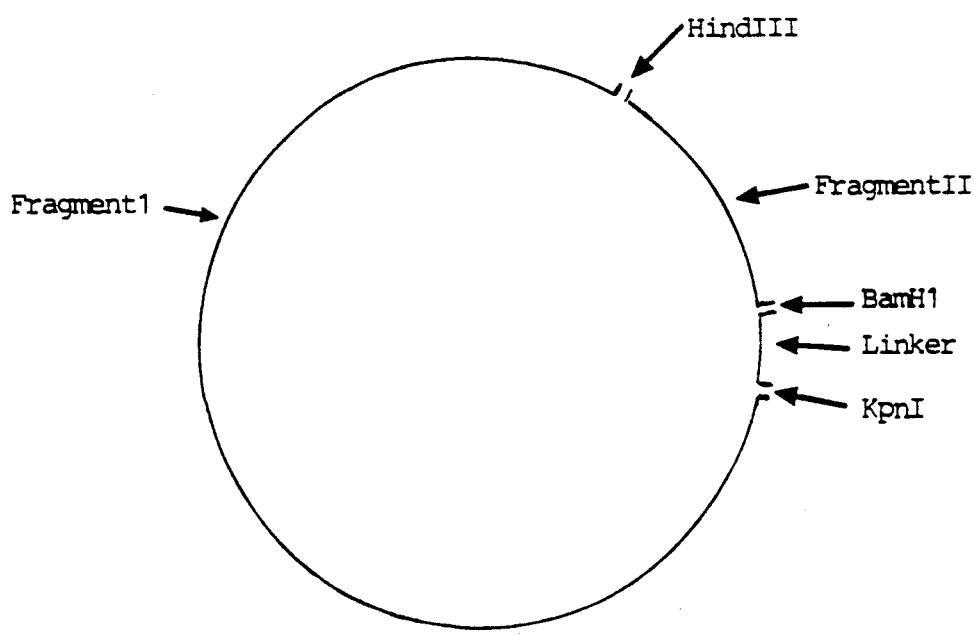

After transformation into *E.coli* the plasmid pTRH02 was isolated (FIG. 9).

Plasmid pTRH02 was used to express a novel hybrid plasminogen activator (H02), believed to have the sequence t-PA 1-91/pro-gly-ser/plasminogen 84-544/t-PA 262-527, in HeLa cells.

EXAMPLE 7

Plasminogen 1-546 /u-PA 137-411(H25)

Construction of plasmid PTRH25

A human urokinase cDNA clone is identified by oligonucleotide probing and is isolated by conventional means (Holmes et al, (1985) Bio Technology 3, 923-929). The cDNA clone is modified by conventional in vitro mutagenesis techniques to incorporate an SstI site at nucleotide 563 and a BglII site in the 3' untranslated region. Amino acids 143 and 144 are then coded by the nucleotide triplets GAG CTC rather than the native GAA TTA (plasmid pTRU2).

To create the hybrid enzyme coding sequence, plasmid pTRH9 (Example 1) is digested with NarI and BglII and the approximately 7 kb fragment I (carrying vector functions and most of the plasmin A chain coding region) is isolated. Plasmid pTRU2 is digested with SstI and BglII and the urokinase B-chain coding fragment II isolated. An oligonucleotide linker III composed of two kinased oligonucleotides Y and Z is made.

```
5'CG CCT TCA TTT CCC TCC TCT CCT CCA
    GAA GAG CT 3'                          (Y)
```

3'GGA AGT AAA GGG AGG AGA GGA GGT
    CTT C 5'                                    (Z)

Figure 10:
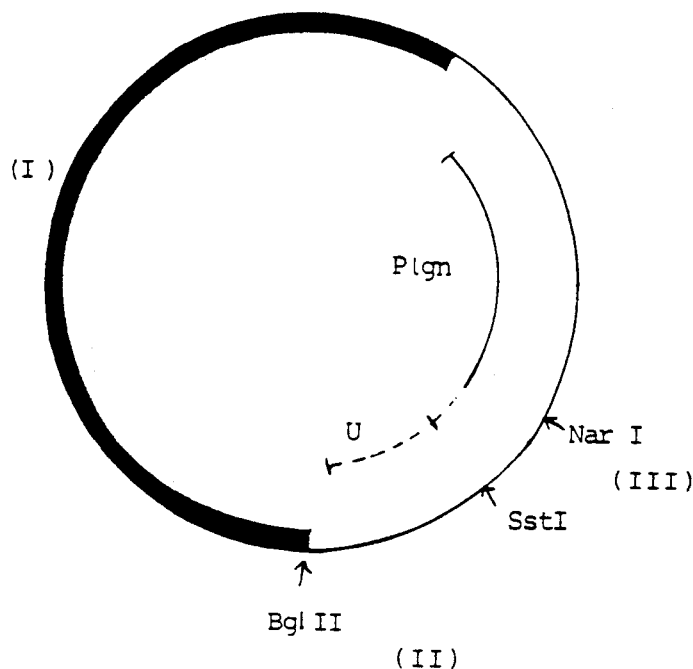

Fragments I and II and linker III are ligated and transformed into *E. coli* HB101 and plasmid pTRH25 isolated (FIG. 10). The new plasmid encodes a novel hybrid enzyme. The structure in the region of the join between fragment I, II and linker III is believed to be as shown in Table 6.

TABLE 6

```
                Nar I
5'... TGT GCG G  CG CCT TCA TTT CCC TCC TCT CCT CCA GAA
3'... ACA CGC C  GC GGA AGT AAA GGG AGG AGA GGA GGT CTT
      cys ala ala  pro ser phe pro ser ser pro pro glu
      541 542 543  544 545 546 137 138 139 140 141 142

<———— plasminogen sequences ————|———— urokinase sequences ————>

Sst I
G AG CT C AAA ...
C TC GA G TTT ...
glu leu lys
143 144 145
```

Plasmid pTRH25 is used to transfect human Hela cells and produce a novel plasminogen activator.

EXAMPLE 8

Expression of plasminogen 1-544/t-PA 262-527 (H204) in Chinese Hamster Ovary cells The plasmid pSV2dhfr was obtained from the American Type Culture Collection (ATCC 37146: Molec. Cell. Biol. 1: 854–864, 1981). The plasmid BPV-MT-Xho was obtained from D. Hamer (National Institutes of Health, Bethesda, Maryland) and contains a version of the mouse metallothionein-I gene (Hamer and Walling (1982) J. Mol. Appl. Genet. 1, 273–288) in which the BglII site just 5' to the translation start point has been converted to an XhoI site by linkering. The t-PA mutein-plasmid pTRE24 has been described previously (EP 0 207 589).

8.1 Construction of an amplifiable expression vector a. Construction of pTRH69

The plasmid pTRH69 was constructed from two fragments A and B, isolated from the plasmid PSV2dhfr and the plasmid BPV-MT-XhoI respectiely.

Figure 11:
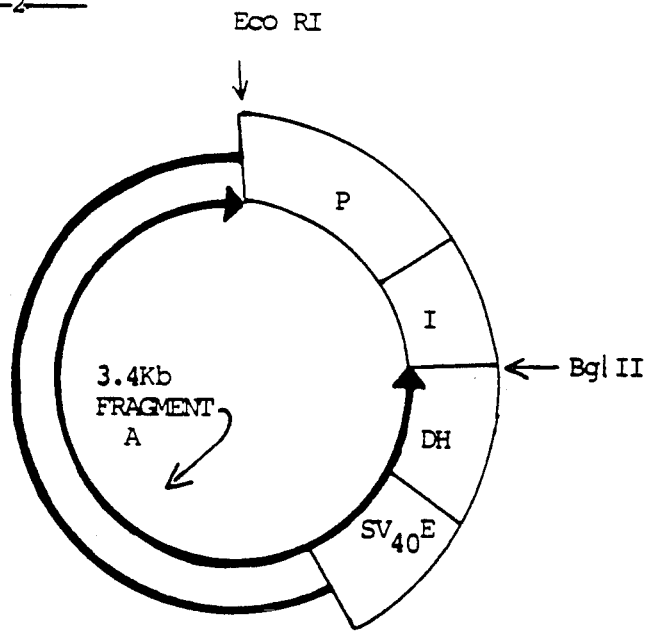

Fragment A: The plasmid PSV2dhfr (FIG. 11) was linearised with EcoRI, blunt ended by infilling and linkered with XhoI linkers. The linearised plasmid was then digested with XhoI and BglII releasing fragment A, (a 3.4 kb fragment encoding the dihydrofolate reductase cDNA and SV40 early promoter sequences).

Figure 12:
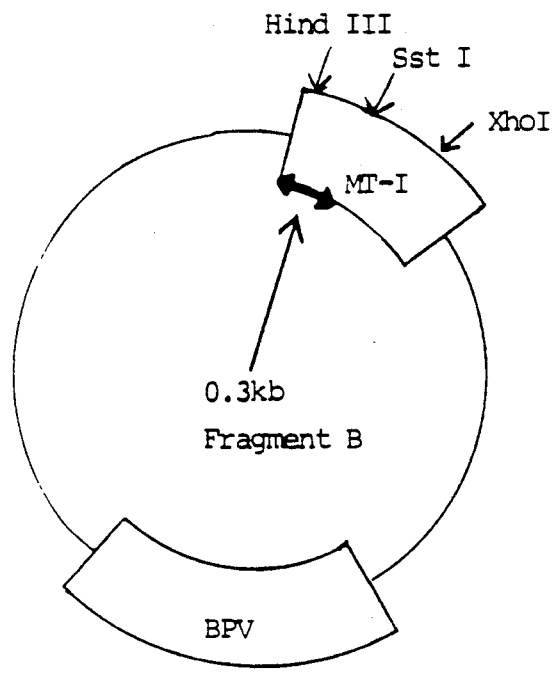

Fragment B: The plasmid BPV MT-XhoI was linearised with SstI, blunt-ended by nuclease digestion and linkered using BglII linkers. The linear plasmid was then digested with HindIII, blunt ended by infilling and linkered with XhoI linkers. The plasmid was then digested with BglII and XhoI releasing fragment B (0.3 kb encoding the 3' metallothionein polyadenylation sequences) (FIG. 12).

Figure 13:
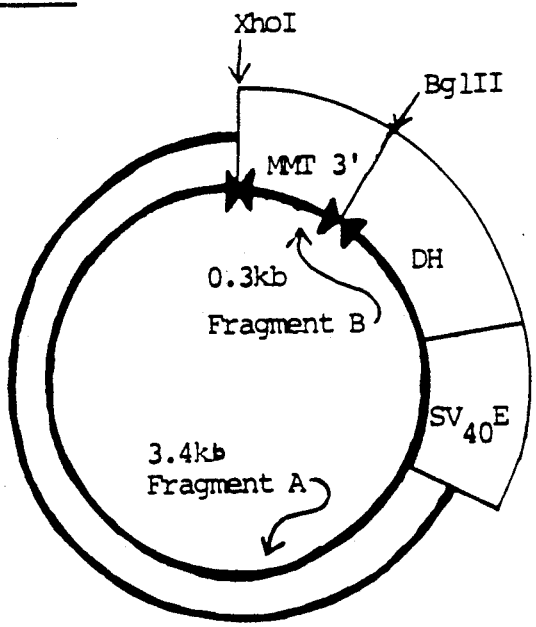

Fragment A and B were isolated by LMP agarose electrophoresis and ligated together. The ligated DNA was tranformed into *E.coli* HB101 and the plasmid PTRH69 was obtained (FIG. 13).

b. Construction of PTRH71

Figure 14:
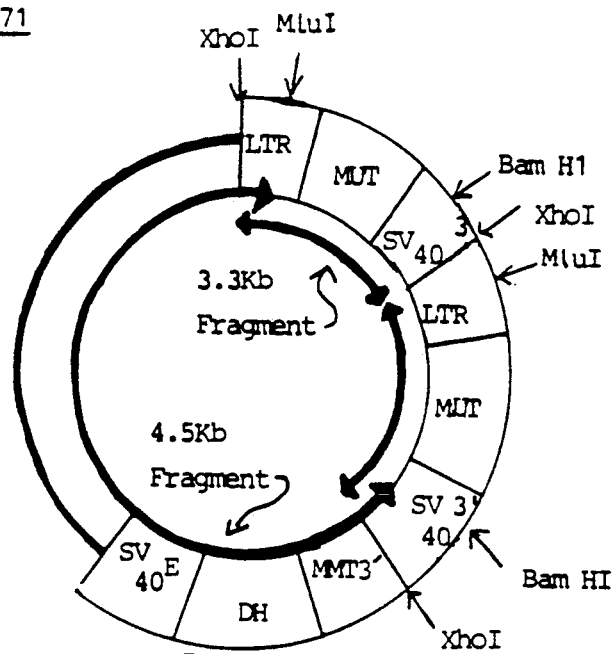

The plasmid pTRH69 was linearised with XhoI and phosphatased. The LMP agarose-purified fragment was ligated with a 3.3Kb XhoI fragment derived from the plasmid pTRE24 which encodes a modified t-PA protein. The ligated DNA was transformed into *E.coli* HB101 and the plasmid pTRH71 was obtained (FIG. 14).

C. Construction of PTRH11

Figure 15:
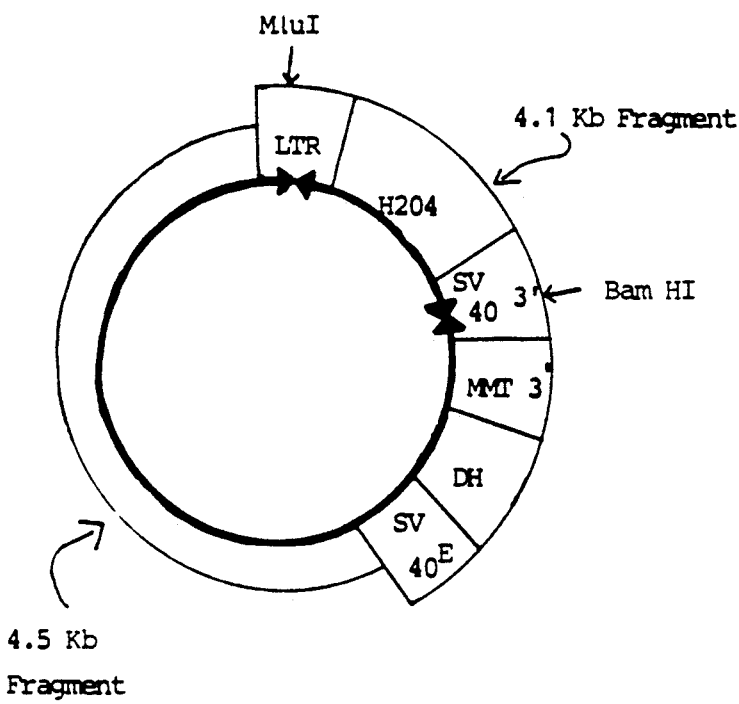
Figure 17F:

The plasmid pTRH71 was digested with MluI and BamHI; a 4.5Kb fragment (comprising the vector functions) was isolated by LMP agarose gel purification and ligated with a 4.1Kb MluI/BamHI fragment isolated from pTRH204 (Example 1) encoding hybrid protein H204. The ligated DNA was transformed into *E.coli* HB101 and the plasmid pTRH11 was obtained (FIG. 15).

8.2 Expression of hybrid protein a. Cell preparation

CHO cells were trypsinised and plated out at $5 \times 10^5$ per 60 mm dish and left in growth medium (Hams F12 nutrient media (041-1765) with 1% stock glutamine (043-5030), 1% stock penicillin/streptomycin (043-5070) and 10% bovine foetal calf serum (013-6290); Gibco, Paisley, Scotland) at 37° C. in a humidified incubator in an atmosphere of 5% $CO_2$/95% air. After 18 hrs the cells were re-fed, after a further 3 hrs the cells were used for DNA transfection.

b. Transfection procedure

The transfection procedure, carried out in growth medium used calcium coprecipitation and glycerol shock as described in DNA Cloning Ed. D. M. Glover (Chap. 15, C. Gorman). Following transfection the cells were maintained in growth medium for 46 hrs under growth conditions (as above) prior to the selection procedure.

c. Selection and Co-amplification

The selection and co-amplification procedure was carried out essentially as described by R. J. Kaufman. (1985) Molecular and Cellular Biology 5, 1750–1759. 46 hrs post transfection the cells were medium changed into selective medium (Eagles MEM (041-1095) with 1% stock sodium pyruvate (043-1360), 1% stock glutamine (043-5030), 1% stock penicillin/streptomycin (043-5070) 0.35% proline (22mg/ml) and 10% dialysed bovine foetal calf serum (063-6300) (Gibco, Paisley, Scotland). The cells were maintained in selective medium for 8–10 days until colonies of dhfr+ cells appeared. When colonies were established the cells were medium changed into selective medium containing methotrexate, (A6770; Sigma, England). After 6 days in selective medium containing methotrexate, the selective medium was modified by replacing the Eagles MEM and sodium pyruvate components with α MEM (041-02561). The methotrexate concentration was initially 0.02 μM and was increased stepwise to 0.05 μM.

d. Detection of hybrid protein H204

During the amplification procedure aliquots of growth medium from growing cells were assayed for plasminogen activator production by fibrin plate and zymography as described by Dodd et al. (1986) Thrombosis and Haemostasis, 55, 94–96. Zymography revealed a fibrinolytically active protein with apparent $M_r$ approximately 100,000 which is consistent with the expected molecular weight of hybrid protein H204.

IV. Purification and post-synthetic modification of hybrid proteins

EXAMPLE A

Purification of plasminogen 1-544/t-PA 262-527 (H204)

200 ml conditioned harvest media obtained from HeLa cell cultures transfected with the plasmid pTR H204 (Example 1) was centrifuged at 9000 g for 30 min and the supernatant retained. It was applied to a column (i.d., 90 mm; h, 220 mm) of Sephadex G25* equilibrated in PBS (Dulbecco A)/0.01% Tween 80 pH 7.4 (PBS/TW). The first approx. 0.35 vt was discarded. The following 500 ml was retained and was chromatographed on zinc chelate-Sepharose (vt-80 ml) and lysine Sepharose (Vt=20 ml) essentially as described previously (Dodd, I. et al (1986a) FEBS Lett 209 13). The major difference was that the purified activator was dissociated from the second column using 0.05M sodium phosphate/0.1M sodium chloride/0.01% Tween 80 pH 7.4 (PST) containing 0.02M ε-aminocaproic acid (ε-ACA). Active fractions eluted by the PST/ε-ACA buffer were identified using the chromogenic substrate H-D-ile-pro-arg-p nitroailide (Dodd, I. et al (1986b) Thromb. Haem. 55 94) and were concentrated by stirred-cell ultrafiltration (YM10, Amicon). The ultrafiltered retentate (2.0 ml) contained 14400 IU and 4800 SU (Dodd, I. et al 1986b). Sodium dodecyl sulphate polyacrylamide gel electrophoresis (SDS PAGE) followed by fibrin zymography (Dodd, I. et al, 1986b) showed that the product contained a major fibrinolytic species with apparent $M_r$ approximately 100000, consistent with the isolation of a $glu_1$ form of the hybrid activator.

*Sephadex and Sepharose are Trade Marks

EXAMPLE B

Synthesis of lys7a tc H204 -protein (two chain plasminogen 78-544/t-PA 262-527)

A preparation of purified H204 protein from Example A that had been buffer-exchanged into PST/10 mg ml$^{-1}$ mannitol/50 μM ε-ACA (89,000 IU, 1.9 ml) was treated with a 0.01 fold molar excess of plasmin at 25° C. for 16 h and then stored at −40° C. Subsequent analysis of the product showed that it contained 68,000 IU and 32,000 SU. The activator had an apparent $M_r$ of approximately 90,000 by SDS PAGE followed by fibrin zymography. The lys,tc nature of the product was confirmed by SDS PAGE followed by immuno blotting using a polyclonal antibody against the t-PA B chain (see methods section).

EXAMPLE C

Preparation of 2-Amino-4-chlorobenzoyl plasminogen 78-544/t-PA 262-527 (two chain) ex.Hela cells Purified $lys_{78}$-tc H204 protein from Example B (3900 SU) in PST/12.5pM ε-ACA/2.5mg ml$^{-1}$ Mannitol (1 ml) was treated with a 5MM solution of 4-amidinophenyl-2'-amino-4'-chlorobenzoate hydrochloride (Example 11 hereinafter) in dimethylsulphoxide (2 μl, 20 eq). After 1 h incubation at 25° C. an inhibition of 40% was noted. A further aliquot (4 μl, 40 eq) of acylating agent solution was added and after a further 1 h at 25° C. 93% inhibition had been obtained. The material was buffer exchanged using a Sephadex G25 (PD 10) column into PST/166 μM ε-ACA/1.66 mg ml$^{-1}$ mannitol (1.35 ml) and frozen at −40° C. The material was deacylated by dilution of stock solution (0.3 ml) with PST (0.2 ml) to give a final solution of PST/100 μM ε-ACA/1 mg ml$^{-1}$ mannitol. The deacylation rate in the above buffer system at 37° C. was $1.05 \times 10^{-4}$ sec$^{-1}$ i.e. a $t_{\frac{1}{2}}$ of 110 min.

EXAMPLE D

Purification of Plasminogen 1-544/t-PA 262-527 (arq$_{275}$→gln)(H205)

515 ml conditioned harvest medium obtained from HeLa cultures transfected with pTR H205 (Example 2) was purified essentially as described in Example A. The hybrid activator was eluted from the lysine Sepharose column using PST/20 mM ε-ACA, was concentrated by ultrafiltration and was then buffer-exchanged into PST/10 mg ml$^{-1}$ mannitol/50 μM ε-ACA (2.0 ml). The product contained 18,000 IU and 6600 SU. Analysis by SDS PAGE followed by fibrin zymography showed the preparation contained two major fibrinolytic species, at apparent Mr approximately 100,000 and 90,000. These are believed to be the $glu_1$ and $lys_{78}$ forms of the hybrid activator.

EXAMPLE E

Purification of plasminogen 1-541/t-PA 262-527 (H37)

510 ml clarified, conditioned harvest medium that had been obtained from HeLa cell cultures that had been transfected with the plasmid pTR H37 (Example 3) was purified essentially as described for H204 in Example A. The hybrid activator was dissociated from the lysine Sepharose column using PST/20 mM ε-ACA, was concentrated by ultrafiltration and was then buffer-exchanged into PST/10 mg ml$^{-1}$ mannitol/50 μM ε-ACA (2.0 ml). The product contained 36,000 IU and 15,000 SU. Analysis by SDS PAGE followed by fibrin zymography showed the preparation contained two major fibrinolytic species, at apparent $M_r$ of approximately 100,000 and 90,000. These are believed to be the $glu_1$ and $lys_{78}$ forms of the activator. SDS PAGE followed by silver staining of non-reduced activator showed the preparation contained major protein bands at $M_r$ approximately 90,000.

Analysis by SDS PAGE followed by immunoblotting using a polyclonal antibody against the t-PA B chain supported the zymography results indicating the presence of $glu_1$ and $lys_{78}$ forms, and, in addition, showed that the product was all two-chain.

EXAMPLE F

Preparation of lys$_{78}$ tc H37 protein (two chain plasminogen 78-541/t-PA 262-527)

Purified H37 protein (0.28 ml, 7400 SU/ml) prepared as described in Example E, containing equal amounts of the glu$_1$ and lys$_{78}$ forms, was treated either with or without an approx. 0.03 fold molar excess of plasmin at 37° C. for 17 h. The amidolytic activity (SU) of both products was the same as that of a control preparation that had been stored at −40° C. Analysis by SDS PAGE followed by fibrin zymography showed that the plasmin-treated H37 protein, and, to a lesser extent, the non-plasmin treated H37 protein, had been converted to the lys$_{78}$ form.

EXAMPLE G

Synthesis of 2-amino-4-chlorobenzoyl-plasminogen 1-541/t-PA 262-527 (two chain) and -plasminogen 78-541/t-PA 262-527 (two chain)

Purified H37 protein from Example F (10 nmoles) in PST/10 mg ml$^{-1}$ mannitol/50 μM ε-ACA (2.0 ml) was treated with 4-amidinophenyl-2'-amino-4'-chlorobenzoate.HCl (2 μmoles, 40 μl) at 25° C. After 60 min the amidolytic activity of the preparation had decreased to <2% of the original activity. The material was buffer-exchanged into PST/10 mg ml$^{-1}$ mannitol/50 μM ε-ACA (3.0 ml) and stored at −40° C.

An aliquot of the acylated product was later diluted with 5 volumes PST/10 mg ml$^{-1}$ mannitol/50 μm ε-ACA and allowed to deacylate at 37° C.

EXAMPLE H

Purification of plasminogen 78-544/t-PA 262-527 (HOO)

500 ml conditioned harvest medium obtained from HeLa cell cultures transfected with the plasmid pTR HOO (Example 4) was clarified by centrifugation (9000 g/30 min) and was purified as described for H204 protein in Example A. The hybrid activator was eluted from the lysine Sepharose column (vt, 49 ml) using PST/20 mM ε-ACA, was concentrated by ultrafiltration and then buffer-exchanged into PST/10 mg ml$^{-1}$ mannitol/50 μM ε-ACA (2.1 ml). The product contained 5,700 IU and 2,700 SU. SDS PAGE followed by fibrin zymography indicated the presence of a major fibrinolytic species with apparent M$_r$ of approximately 90,000. SDS PAGE followed by staining for protein or immunoblotting using polyclonal antibody against the t-PA B-chain revealed the material was in the two-chain form. These results are consistent with the isolation of lys$_{78}$ tc hybrid plasminogen activator.

EXAMPLE I

Purification of t-PA 1-91/pro-gly-ser/plasminogen 84-544/t-PA 262-527 (HO2)

380 ml Conditioned harvest medium obtained from HeLa cell cultures transfected with the plasmid pTR H02 (Example 6) was clarified by centrifugation (9000 g/30 min) and purified essentially as described for H204 protein in Example A. The hybrid activator was dissociated from the lysine Sepharose column (Vt, 55 ml) using PST/20 mM ε-ACA. The eluate was concentrated by ultrafiltration and then buffer-exchanged into PST/10mg ml$^{-1}$ mannitol/50 με-ACA (2.0 ml) to give the product. This contained 42,000 IU and 20,400 SU. SDS PAGE followed by fibrin zymography showed a major fibrinolytic species at M$_r$ of approximately 100,000. SDS PAGE followed by protein staining or immunoblotting using a polyclonal antibody against the t-PA B-chain showed that the hybrid enzyme was in the two-chain form.

EXAMPLE J

Synthesis of 2-amino-4-chlorobenzoyl t-PA 1-91/pro-gly-ser/plasminogen 84-544/t-PA 262-527 (two chain)

H02 protein (1 ml, 0.25 nmoles) purified as described in Example I was treated with 4-amidinophenyl-2'-amino-4'-chlorobenzoate.HCl (1.25 μl, 25 μmoles) at 25° C. After 1 h 93% of the amidolytic (S2288) activity of the preparation had been lost. After addition of another 25 nmoles acylating agent and a further incubation for 15 min the material was buffer-exchanged into PST/10mg ml$^{-1}$ mannitol/50 μm ε-ACA (2.2 ml), aliquoted and stored at −70° C.

Subsequently, an aliquot of the product was diluted with 1 volume 0.1 M Tris/0.15M NaCl/20% (v/v) glycerol/0.01% Tween 80 pH 7.4 and allowed to deacylate at 37° C. The rate of deacylation was determined by assaying the S2288 activity of the solution. The deacylation rate constant of the acylated protein under the described conditions was $3.9 \times 10^{-4}$ sec$^{-1}$.

EXAMPLE K

Purification of t-PA 1-50/t-PA 88-91/pro-gly-ser/plasminogen 84-544/t-PA 262-527 (H01)

2.0 ml conditioned harvest medium from HeLa cell cultures transfected with the plasmid pTR H01 (Example 5) was buffer-exchanged into PST/10mg ml$^{-1}$ mannitol/50 μM ε-ACA (3.0 ml) and concentrated by ultrafiltration (Centricon* 10, Amicon) to about

*Centricon is a Trademark 0.45 ml. The concentrate contained 520 IU/ml; analysis by SDS PAGE followed by fibrin zymography revealed a major fibrinolytic species at apparent M$_r$ approx. 10000.

The hybrid activator was purified by incubating the 0.45 ml solution with 0.2 ml lysine Sepharose suspension, removing the supernatant, washing the gel with PST and finally eluting the adsorbed activator with PST/20 mM ε-ACA, to yield about 0.8 ml solution containing 60 IU/ml partially-purified H01 protein.

EXAMPLE L

Purification of plasminogen 1-544/t-PA 262-527 (H204) produced by Chinese Hamster Ovary cells CHO cells transfected with pTRH11 (Example 8.1c.) and selected for survival in methotrexate at 0.05 μM (Example 8 ) were harvested (25 ml per175 cm$^2$ flask) for 24 h in αMEM (041-02561) containing 1% penicillin/streptomycin (043-5070), 1% glutamine (043-5030) (Gibco, Paisley, Scotland), and 3 mM sodium butyrate (9686730F; BDH Chemical Ltd., Poole, England). 1400 ml of harvest medium was collected.

The harvest medium was clarified by centrifugation (9000 g/30 min) and purified on zinc chelate Sepharose (Vt, 230 ml) and lysine sepharose (Vt, 46 ml) using essentially the same method as that described for protein H204 in Example A. The major difference was that the lysine Sepharose column was noted eluted with the ε-ACA- containing buffer, but with the following, in succession:
a. 0.02M Tris/0.5M NaCl/0.01% Tween 80 pH 7.4
b. as a. but also containing 0.1M L-arginine
c. as a. but also containing 0.2M L-arginine
d. as a. but also containing 0.3M L-arginine
e. as a. but also containing 0.4M L-arginine
f. as a. but also containing 0.5M L-arginine Analysis of the individual fractions that had been collected showed that both endogenous CHO-cell t-PA and protein H204 had adsorbed to the lysine Sepharose column, and both had been dissociated by the arginine—containing buffers. Analysis by SDS PAGE followed by fibrin zymography further showed that the majority of purified protein H204 had clearly been separated from the endogenous CHO cell t-PA, the latter being dissociated by a lower concentration of arginine. The apparent $M_r$ of H204 by SDS PAGE followed by fibrin zymography was approx. 100,000 (with a minor species at approx. 90000), clearly different from the endogenous CHO t-PA, at $M_r$ approx. 65000.

Further analysis of H204 protein by Western blotting using a polyclonal antibody against t-PA B-chain showed that the bulk of the protein was in the two chain form.

Example M

Synthesis of 2-amino-4-chlorobenzoyl plasminogen 1-544/t-PA 262-527 and 2-amino-4-chlorobenzoyl plasminogen 78-544/t-PA 262-527 ex. CHO cells 10,000 IU purified two-chain H204 protein from CHO cells (Example L) in PST/10 mgml$^{-1}$ mannitol/50 μM ε-ACA (1 ml) was treated with 4-amidinophenyl-2′-amino-4′-chlorobenzoate.HCl (20 mM, 2.5 μl) for 1 h at 25° C. followed by an additional 2.5 μl aliquot for a further 20 min. The acylated H204 was buffer-exchanged into PST/10 mgml$^{-1}$ mannitol/50 μM ε-ACA (1.5 ml) using Sephadex G25 and aliquoted. Fibrin plate assay indicated that the acyl product contained 3600 IU/ml. The deacylation rate constant was determined as $1.2 \times 10^{-4}$ sec$^{-1}$.

Analysis of the acylated product by SDS PAGE followed by fibrin zymography showed two definite species, with apparant $M_r$ approximately 100000 and 90000. The former is likely to be the glu$_1$ form of acylated H204. The latter is most likely the lys$_{78}$ form.

V. Preparation of Derivatives of the Invention

Methods for Examples 9-17

(a) Chromogenic substrate assay

Urokinase and t-PA were assayed against the chromogenic substrates (Kabivitrum, Sweden) S-2444 and S-2288, respectively at a substrate concentration of 1 mM in 0.1M triethanolamine.HCl pH 8.0 at 25° C. An SU is defined as the amount of activity that gives an O.D. increase of 0.001/min in 0.5 ml substrate in a 1 cm pathlength cell.

(b) Rate constant determinations

The pseudo first order rate constant is determined by hydrolysing the acyl-enzyme under physiological conditions, i.e. in isotonic aqueous media at pH 7.4 and at 37° C. At regular intervals aliquots are withdrawn and incubated with a chromogenic substrate and the rate of conversion of the substrate measured as indicated above.

The hydrolysis is followed until such time as the rate of conversion of substrate reaches a maximum. The rate constant k may then be calculated by plotting:

$Log_e (1 - A_t/A_{max})$ against t where $A_{max}$ is the maximum rate at which an aliquot converts substrate and $A_t$ is the rate at which an aliquot converts substrate at time t.

Preferably such rate constants are calculated by computerised non-linear regression analysis, fitting the $A_t$ and time data to the equation:

$A_t = A_o^* (A_{max} - A_o)(1 - e^{-kt})$ where $A_o$ is the activity of the acyl-enzyme preparation before deacylation.

EXAMPLE 9

4′-Amidinophenyl 2-amino-4-fluorobenzoate (a) 2-Methyl-5-fluoroacetanilide

5-Fluoro-2-methylaniline (6.26 g, 50 mmol) and triethylamine (7.26 g, 10 ml, 72 mmol) were dissolved in dichloromethane (50 ml). This mixture was added dropwise to an ice-cooled solution of acetyl chloride (3.925 g, 3.55 ml, 50 mmol) in dichloromethane (100 ml) under an atmosphere of nitrogen. The solution was allowed to warm to room temperature and stirred for 3 h. The organic layer was then washed successively with 10% sodium hydrogen carbonate solution (50 ml), 2M hydrochloric acid (50 ml) and saturated sodium sulphate solution (50 ml). The organic layer was dried, filtered and evaporated and the residual solid purified by column chromatography (70 g silica in dichloromethane→10% ethyl acetate/90% dichloromethane) to leave the title compound (5.41 g, 65%).

m.p.: 127° C. ex ethanol and water
$^1$H nmr (CDCl$_3$) δ: 6.5-7.8 (4H, m, aryl-H+N—H̲), 2.15 (6H,s,CH$_3$+COCH$_3$)
IR $\mu_{max}$ (Nujol): 3270, 1650, 1600, 1530, 1285, 1250, 860, 800 and 610 cm$^{-1}$
Found: C 64.40, H 6.26, N 8.27. C$_9$H$_{10}$NOF requires: C 64.66, H 6.03, N 8.27%.

(b) 2-(Methylcarbonylamino)-4-fluorobenzoic acid

2-Methyl-5-fluoroacetanilide (Example 9(a)) (2.0 g, 10 mmol) was dissolved in water (50 ml) and potassium permanganate (2.25 g, 14 mmol) was added. The reaction was stirred and heated to reflux until the purple colour disappeared. Two more aliquots of the oxidant (2×1.125 g) were added at approximately 2 h intervals.

The reaction was allowed to cool after 6 h and the solution was brought to basic pH. It was then filtered through celite and the aqueous solution was acidified. The aqueous layer was extracted with ethyl acetate (50 ml) which was then dried, filtered and evaporated to leave the title compound (0.5 g, 22%).

m.p.: (sublimes above 140° C.)from ethanol and water
$^1$H nmr (CDCl$_3$) δ: 11.4 (1H,br s, CO$_2$H), 8.2 (2H, m, aryl-H̲), 6.8 (1H, m, aryl-H̲), 2.15 (3H, s, COCH$_3$)
IR $\mu_{max}$ (Nujol): 3470, 3410, 2500-3400, 1705, 1670 and 1615 cm$^{-1}$
Found: C 54.49, H 4.34, N 6.38. C$_9$H$_3$NFO$_3$ requires: C 54.83, H 4.09, N 7.10%.

(c) 4-Fluoroanthranilic acid 2-(Methylcarbonylamino)-4-fluorobenzoic acid (Example 9(b)) (0.45 g 2.3 mmol) was suspended in water (15 ml) and 5M sodium hydroxide solution was added (1.8 ml, 9 mmol).

The solution was heated at reflux for 24 h and then allowed to cool. The basic solution was extracted with dichloromethane, which was discarded, and acidified. The acidic solution was extracted with ethyl acetate (2×25 ml), and this was dried, filtered and evaporated to leave the title compound (0.36 g, 100%).

m.p.: 193°–5° C. from ethanol and water $^1$H nmr (CDCl$_3$/d$^6$DMSO) δ: 8.0 (4H, m on br hump, aryl-$\underline{H}$+2×N$\underline{H}$ and CO$_2\underline{H}$), 6.5 (2H, m, aryl-$\underline{H}$)

IR $\mu_{max}$ (Nujol): 3500, 3380, 2500–3400, 1665, 1600, 1570, 1490, 1225, 1180, 1145, 980, 890, 835, 760 and 620 cm$^{-1}$ Found: C 54.19, H 3.94, N 8.83. C$_7$N$_6$NO$_2$F requires: C 54.20, H 3.90, N 9.03%.

(d) 4'-Amidinophenyl 2-amino-4-fluorobenzoate

2-Amino-4-fluorobenzoic acid (Example 9(c)) (320 mg) was dissolved in pyridine (2 ml) and 4-amidinophenol (364 mg) was added. Dicyclohexylcarbodiimide (425 mg) was added and the mixture stirred at room temperature under nitrogen for 18 h. A mixture of product and dicyclohexylurea was precipitated. This was triturated with ethanol (10 ml) and filtered. The product was precipitated by addition of diethylether to the alcoholic solution. The title compound (133 mg, 21%) was isolated as flaky white crystals.

m.p: >250° C. from ethanol and ether $^1$H nmr (d$^6$DMSO) δ: 9.5 (4H, br s, amidine-N$\underline{H}$), 8.0 (3H, m, amidine aryl-$\underline{H}$+benzoate aryl-$\underline{H}$), 7.5 (2H, d, J=8 Hz, amidine aryl-$\underline{H}$), 7.0 (2H, s, aryl-$\overline{NH_2}$), 6.6 (1H, m, aryl-$\underline{H}$), and 6.2 (1$\overline{H}$, m, aryl-$\underline{H}$).

IR $\mu_{max}$ (Nujol): 3470, 3370, 3330, 2500–3500, 1700, 1680, 1630, 1580, 245, 1210, 1180, 1040, 745, 700 cm$^{-1}$ Found: C 53.76, H 4.23, N 13.35. C$_{14}$H$_{13}$N$_3$O$_2$FCl. ¼ H$_2$O requires: C 53.51, H 4.33, N 13.37%.

EXAMPLE 10

4'-Amidinophenyl 2-amino-4-chlorobenzoate

Recrystallized commercial 2-amino-4-chlorobenzoic acid (345 mg) and 4-amidinophenol (345 mg) were dissolved in pyridine (5 ml). Dicyclohexylcarbodiimide (824 mg, 2eq) was added and the mixture stirred at room temperature under an atmosphere of dry nitrogen for 3d. In this time a solid was formed. This was isolated by filtration and was found to be a mixture of the title compound and dicyclohexylurea. The material was triturated with chloroform (6×10 ml) to remove the urea. This left the title compound (81 mg, 12%).

m.p: 230°–2° C.

$^1$H nmr (d$^6$DMSO) δ: 9.20 (4H,s, aryl-amidine-N$\underline{H}$), 7.90 (3H, m, aryl-$\underline{H}$), 7.52 (2H, d, J=9 Hz, aryl-$\underline{H}$), 6.95 (3H, m, aryl-$\underline{H}$+$\overline{NH_2}$), 6.65 (1H, m, aryl-$\underline{H}$)

IR μmax (Nujol): 3460, 3160, 1710, 1680, 1610, 1220, 1180, 1040 cm$^{-1}$.

Found: C 51.79, H 4.19, N 12.57. C$_{14}$H$_{13}$N$_3$Cl$_2$O$_2$ requires: C 51.55, H 4.02, N 12.88.

EXAMPLE 11

4'-Amidinophenyl 2-amino-4-bromobenzoate (a) 2-Amino-4-bromotoluene

4-Bromo-2-nitrotoluene (13.5 g, 62.5 mmol) and granulated tin (11.25 g, 95 mmol) were placed in a round bottomed flask to which concentrated hydrochloric acid (25 ml) was added in small (ca 5 ml) aliquots. A gentle reaction was evident during this addition period. When all the acid had been added the reaction mixture was heated and stirred at about 100° C. for 4 h. The solution was allowed to cool and a solution of sodium hydroxide (18.75 g) in water (32 ml) was added. The solution was heated at 100° C. for 1 h. After cooling, water (200 ml) was added and the solution was filtered. The aqueous filtrate was extracted with diethyl ether (200 ml). The filtered salts were also extracted with diethyl ether (200 ml). The combined organic layers were dried, filtered and evaporated to leave an oil. This was purified by distillation (112° C. at 4 mm Hg) to leave the title compound (6.76 g, 58%).

$^1$H nmr (CDCl$_3$) δ: 6.8 (3H, m, aryl-$\underline{H}$), 3.6 (2H, s, N$\underline{H}_2$), and 2.1 (3H,s,C$\underline{H}_3$).

(b) 2-Methyl-5-bromoacetanilide

This was synthesized in the same manner as the fluoro-analogue (Example 9(a)) in 96% yield from 2-amino-4-bromotoluene (Example 11(a)). The preparation did not require any column chromatography.

m.p.: 108°–110° C. from dichloromethane and 40°–60° petroleum ether, $^1$H nmr (CDCl$_3$) δ: 7.8 (2H, m, aryl-$\underline{H}$+N-$\underline{H}$), 7.1 (2H, m, aryl-$\underline{H}$), 2.15 (6H, s, C$\underline{H}_3$ and COC$\underline{H}_3$)

IR $\mu_{max}$ (Nujol): 3250, 1670, 1650, 1580, 1530, 1400, 1380, 1290, 1230, 1190, 1130, 860, 800, and 700 cm$^{-1}$ Found: C 48.00, H 4.43, N 6.16. C$_9$H$_{10}$NOBr requires: C 47.39, H 4.42, N 6.14%.

(c) 2-(Methylcarbonylamino)-4-bromobenzoic acid

This material was produced in 10 mmol scale from 2-methyl-5-bromoacetanilide (Example 11(b)) in the same way as the fluoro-analogue (Example 9(b)). A yield of 58% was obtained.

m.p: 212°–5° C. from methanol and water $^1$H nmr (CDCl$_3$/d$^6$DMSO) δ: 11.4 (2H,br s, N$\underline{H}$ and CO$_2\underline{H}$), 9.3 (1H, m, aryl-$\underline{H}$), 8.2 (1H, m, aryl-$\underline{H}$), 7.4 (1H, m, aryl-$\underline{H}$), 2.3 (3H, s, aryl-C$\underline{H}_3$)

IR $\mu_{max}$ (Nujol): 3250, 1670, 1650, 1580, 1520, 1290, 860 and 800 cm$^{-1}$ Found: C 41.43, H 3.08, N 5.31. C$_9$H$_8$BrNO$_3$ requires: C 41.89, H 3.12, N 5.43%.

(d) 4-Bromoanthranilic acid

The title compound was prepared in 48% yield from 2-(methylcarbonylamino)-4-bromobenzoic acid (Example 11(c)) in the same manner as the fluoro-analogue (Example 9(c)).

$^1$H nmr (CDCl$_3$/d$^6$DMSO) δ: 8.1 (3H, s, CO$_2\underline{H}$+N$\underline{H}_2$), 7.6 (1H, d, J=8 Hz, aryl-$\underline{H}$), 6.8 (1H, m, aryl-$\underline{H}$), 6.6 (1H, M, aryl-$\underline{H}$).

(e) 4'-Amidinophenyl 2-amino-4-bromobenzoate

2-Amino-4-bromobenzoic acid (Example 11(d)) (0.90 g) and 4-amidinophenol (0.718 g) were dissolved in pyridine (10 ml). Dicyclohexylcarbodiimide (1.71 g, 2 eq) was added. The reaction was stirred at room temperature under an atmosphere of dry nitrogen for 2d. It was then filtered and the solid obtained was found to be a mixture of the title compound and dicyclohexylurea. The material was repeatedly triturated with chloroform (6×20 ml) before being isolated by filtration and evaporation. The pure title compound was obtained (144 mg, 9%).

$^1$H nmr (d$^6$DMSO) δ: 9.20 (4H, 6r s, amidine-N$\underline{H}$), 7.90 (3H, m, aryl-$\underline{H}$), 7.55 (2H, d, J=6 Hz, aryl-$\underline{H}$), 7.1 (1H, s, aryl-$\underline{H}$), 6.95 (2H, br s, N$\underline{H}_2$), 6.80 (1H, m, aryl-$\underline{H}$)

IR $\mu_{max}$ (Nujol): 3450, 3200, 1710, 1680, 1610, 1230, 1180, 1040 cm$^{-1}$.

EXAMPLE 12

General Methods for the Preparation of Active-centre Acylated Derivatives of Tissue Plasminogen Activator and Urokinase Two-chain t-PA (prepared as in Browne, et al., Thrombosis and Haemostasis 54, 422–424 (1985)) and UK (Serono, Freiburg, W. Germany) stock were dissolved in a 10:1 mixture of 0.05M sodium phosphate, 0.1M sodium chloride, 0.01% v/v Tween 80* pH 7.4:0.25M lysine, 100 mg/ml D-mannitol, 10 mM 6-aminohexanoic acid pH 7.4 (1.1 ml) to give final concentrations of enzyme between 50,000 and 100,000 SU ml$^{-1}$. This material was treated with a 6–10 mM solution of acylating agent in dimethylsulphoxide. The acylations were generally conducted at 0° C. overnight, although on occasion, the temperature was raised to 25° C. for up to 1 h to permit greater than 90% acylation to take place as judged by chromogenic substrate assay. The acyl-enzyme was desalted into 0.05M sodium phosphate, 0.1M sodium chloride, 0.01% v/v Tween 80, pH 7.4 (PST Buffer) by passage through a prepacked PD10 column (Sephadex G25M, Pharmacia). The acyl-enzyme was collected into PST buffer (2 ml). Several aliquots (0.1 ml) of this stock solution were diluted into prewarmed (37° C.) buffer (0.9 ml) and the rate of deacylation was determined by the return of amidolytic activity as described in the methods section and with the results given in Table 7.

*Tween 80 is a tradename for a detergent comprising polyoxythylene sorbitan monooleate having a molecular weight of approximately 1300 and containing approximately 18 to 22 oxyethylene units.

phate buffer containing 1.0 mM 6-aminohexanoic acid. The product was stored in solution at −70° C. Deacylation of the product, diluted 1:10 vv in phosphate buffer at 37° C., indicated that the acyl-enzyme deacylated with an average first order rate constant of $2.64 \pm 0.09 \times 10^{-4}$ sec$^{-1}$ (half life: 43.8 min).

EXAMPLE 14

2-Amino-4-fluorobenzoyl derivative of a conjugate of urokinase with the active centre of human plasmin The urokinase-plasmin conjugate of Example 13 above (209900 SU/ml, 2.1 ml in the phosphate buffer referred to above but containing 5.0 mM 6-aminohexanoic acid) was treated with a solution of the acylating agent of Example 9 above (41 μl of 50 mM in dry dimethylsulphoxide) and incubated at 25° C. After 45 min, a further 10.5 μl of 50 mM acylating agent were added to bring the final concentration to 1.25 mM. After a further 40 min at 25° C., the amidolytic activity of the mixture had declined to 3.5% of the initial activity and the product was gel filtered on a small column of Sephadex G25M into the above phosphate/6-aminohexanoic acid buffer (3.4 ml). The product was stored in frozen solution at −196° C. Deacylation at 37° C. in phosphate buffer gave a mean first order deacylation rate constant of $1.0 \times 10^{-4}$ sec$^{-1}$. Two other batches of this material, prepared in a similar fashion, gave acyl-enzymes with deacylation rate constants of 0.94 and $1.43 \times 10^{-4}$ sec$^{-1}$ (average half life: 101.6 min).

EXAMPLE 15

TABLE 7

| Acylating Agent | Acyl-Urokinase | | Acyl-Tissue Plasminogen Activator | |
|---|---|---|---|---|
| | Number of equivalents of acylating agent used in preparation | Half life for deacylation min. (No of determinations) | Number of equivalents of acylating agent used in preparation | Half life for deacylation min. (No of determinations) |
| 4'-Amidinophenyl 2-amino-4-fluorobenzoate | 3 | 97 (2) | — | — |
| 4'-Amidinophenyl 2-amino-4-chlorobenzoate | 3 | 59 (4) | 3 | 110 (4) |
| 4'-Amidinophenyl 2-amino-4-bromobenzoate | 12 | 34 (4) | 12 | 72 (4) |

EXAMPLE 13

2-Amino-4-chlorobenzoyl derivative of a conjugate of urokinase with the active centre of human plasmin A solution of the conjugate between iminothiolane-treated human urokinase and the acyl-enzyme 4-[N-2-(3-[2-pyridyldithio]-propionyl)aminoethylamino]benzoyl human plasmin (Example 10 of EP-A-0155388, 0.25 ml in 0.5M l-arginine, 0.02M trishydroxymethyaminomethane, 0.5M sodium chloride, 0.01% w/v Tween 80 detergent pH 7.4) was diluted to 1.0 ml with 0.05M sodium phosphate, 0.1M sodium chloride, 0.01% w/v Tween 80 pH 7.4 (phosphate buffer). This solution was assayed against substrate S-2444 and contained 31500 SU/ml. A solution of the acylating agent of Example 10 (20 μl of 10 mM in dimethylsulphoxide) was added and the mixture held at 0° C. for 2 h after which time the activity had declined to 12440 SU/ml. A further 20 μl of acylating agent was added and incubation continued at 25° C. for 30 min, the product being then held on ice. The final activity was 1875 SU/ml (6%). The mixture was gel filtered on a small column of Sephadex G-25M (PD10 column, Pharmacia) into phos-

2-Amino-4-chlorobenzoyl des (cys$_{51}$-asp$_{87}$) rt-PA

Des (cys$_{51}$-asp$_{87}$) rt-PA (Example 4B of EP-A-0 207 589) was produced from mouse C127 cells in a two chain form and was purified essentially as described for native rt-PA (Dodd et al Febs Lett., 1986, 209, 13–17). Purified t-PA mutein (1.5 ml; 5,300 SU/ml; approx. 1.5 nmol) in 0.05M phosphate/0.1M NaCl/0.01% Tween 80/10 mg ml$^{-1}$ mannitol/1 mM EACA pH 7.4 (PST/ME) was mixed with 4'- amidinophenyl 2-amino-4-chlorobenzoate (Example 10 1.5 μl; 10 mM in DMSO). After 30 min at 25° C. the activity of the solution was 2100 SU/ml, equivalent to 60% inhibition. Further gradual additions of acylating agent was made such that the final acylating agent concentration was 60 μM. At an overall incubation period of 135 min, the residual activity in the solution was 410 SU/ml, equivalent to 92% inhibition. Excess acylation agent was removed by buffer-exchange into PST/ME (2.6 ml) using Sephadex G25. The material eluting in the void volume (2-amino-4-chlorobenzoyl t-PA mutein) was stored at −70° C.

A sample of the product was later deacylated by diluting it with 2 ml PST, incubating at 37° C. and monitoring the amidolytic activity as described in the Methods Section. 78% of the original amidolytic activity returned. In subsequent batches the mean deacylation rate constant was found to be $7.8 \times 10^{-5} \text{sec}^{-1}$ (half life: $149 \pm 8$ min, 70 determinations).

EXAMPLE 16

2-Amino-4-chlorobenzoyl ($lys_{78}$ plasmin A chain) $ile_{276}$ t-PA

Purified $lys_{78}$ plasmin A chain/$ile_{276}$ t-PA hybrid plasminogen activator synthesized essentially as described in Examples 1 and 2 of EP-A-0 155 387 (9.2 ml; 6,000 SU/ml, approx. 40 nmol) in PST/ME Buffer (Example 15) was mixed with 4'-amidinophenyl 2-amino-4-chlorobenzoate (Example 10) (50 µl; 10 mM in DMSO). After 60 min incubation at 25° C. the residual amidolytic activity of the preparation was 1900 SU/ml, equivalent is to 3% of the original activity. Excess acylating agent was removed by buffer-exchange into PST/ME using a column ($245 \times 26$ mm) of Sephadex G25. The acylated hybrid plasminogen activator eluted at the void volume of the column and it was stored at $-70°$ C.

A sample of the acylated hybrid plasminogen activator was subsequently diluted with 19 vol. PST and incubated at 37° C. The amidolytic activity of the preparation was monitored as described in in the methods Section. The results indicated that 96% of the hybrid was in the acylated form prior to deacylation. In subsequent batches the deacylation rate constant was found to be $8.9 \times 10^{-5} \text{sec}^{-1}$ (half life: $130 \pm 5$ min, mean of 11 determinations).

EXAMPLE 17

The 2-amino 4-fluorobenzoyl derivative of a conjugate of low molecular weight urokinase with the active centre of human plasmin A conjugate was prepared between thiolated human urokinase and the acyl-enzyme 4-[N-2-(3-[2-pyridyldithio]-propionyl aminoethylamino]benzoyl human plasmin as described in Example 10 of EP-A-0155388 except that low molecular weight (33 kilodalton) urokinase was employed instead of the high molecular weight form (54 kilodalton). The two forms are distinguished by the absence, in the 33K molecule, of the N-terminal 135 amino-acids. The conjugate had a molecular weight of about 110 kilodaltons. This conjugate (0.8 ml in 0.5M L-arginine, 0.5M sodium chloride, 0.02M trisaydroxymethylaminomethane, 0.01% w/v tween 80 detergent pH 7.4, activity: 290,000 SU/ml against S-2444) was treated with the acylating agent of Example 9 (40 µl of 20 mM in dry dimethylsulphoxide) for 30 min at 25° C. Partial ( 80%) acylation occurred and the product was gel-filtered into the phosphate/6-aminohexanoic acid buffer described in Example 6 above (3.4 ml) and acylation repeated using the same conditions as above. The activity decreased to 2.5% of the starting level and the product was reduced in volume to 1.5 ml by centrifugal concentration (Amicon C-30, 2000 g, 45 min, 4° C.). After gel filtration as described above, the product (3.4 ml) was stored at $-196°$ C. Deacylation at 37° C. in phosphate buffer gave a mean first order deacylation rate constant of $1.12 \times 10^{-4} \text{sec}^{-1}$ (average half-life: 103.3 min). A second set of determinations gave a value of $0.97 \times 10^{-4} \text{sec}^{-1}$.

BRIEF DESCRIPTION OF THE DRAWINGS (N.B. Not to scale)

FIG. 1a Structure of pTRH6

■■ = pUCs sequences
— = plasminogen cDNA sequences
← = restriction sites

FIG. 1b Structure of pTRH3

Figure 2:
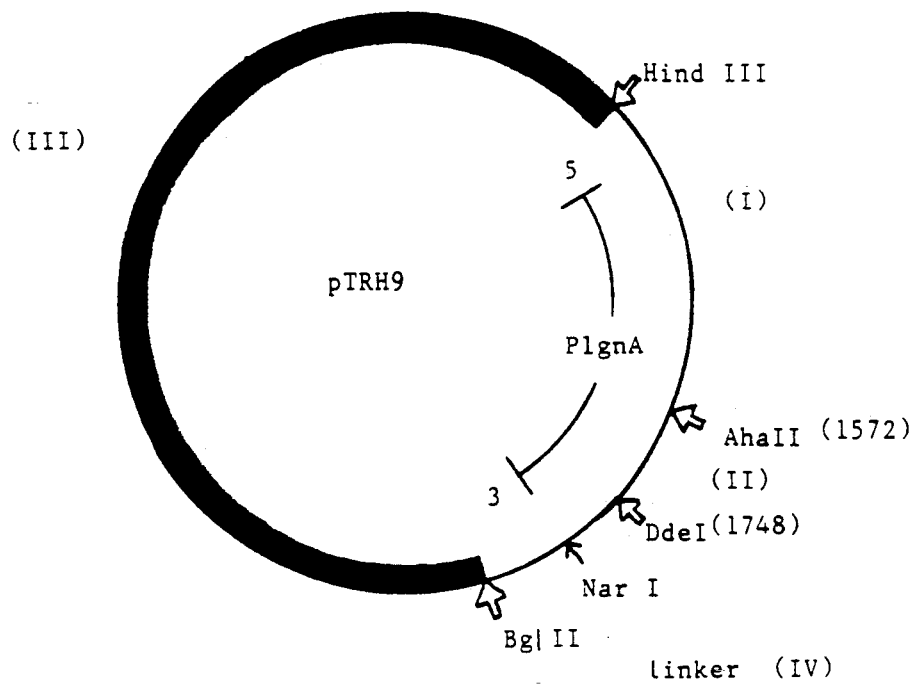

■■ = pTRE12 sequences
— = plasminogen cDNA sequences (Hind III at 5' end, BGIII at 3' end).
= restriction sites used in construction FIG. 2 Structure of pTRH9

Fragments (I) to (III) and linker (IV) are indicated.
■■ = pTRE12 D Nar Sequences
— = insert Sequences
PlgnA = plasminogen A chain coding region
◊ = restriction sites used in construction
← = other restriction sites
|—| = protein coding regions FIG. 3 Structure of pTRH20

Figure 4:
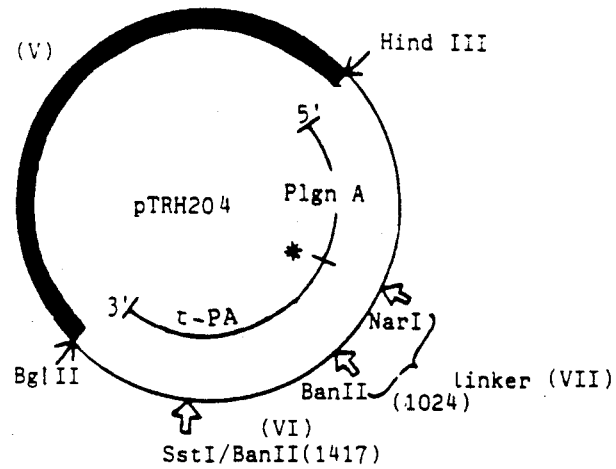

■■ = vector sequences
— = insert DNA
◊ = restriction sites used in contruction
← = other restriction sites
* = linking amino acid sequence
|—| = protein coding regions
Plgn A = plasminogen A chain-coding region
$t_A$ = t-PA A chain coding region
$t_B$ = t-PA B chain coding region FIG. 4 Structure of pTRH204

Fragments (V) (SstI-NarI), (VI)(BanII-SstI) and linker (VII)(NarI-BanII) are indicated.
■■ = vector sequences
— = insert DNA
◊ = restriction sites used in construction
← = other restriction sites
* = serine equivalent to plasminogen serine 545/t-PA serine 262 at junction
|—| = protein coding regions
PlgnA = plasminogen A chain coding region (glu-1 to pro-544)
t-PA = t-PA coding region (thr-263 to pro-527)

FIG. 5 Structure of pTRH37

Fragments (IX)(SstI-BstXI),(X)(BstXI-AvaII) and linker (XI) (AvaII-BanII) are indicated.
■■ = vector sequences
— = insert DNA
◊ = restriction sites used in construction
← = other restriction sites
|—| = protein coding regions
Plgn = plasminogen coding sequences ($glu_1$-$cys_{541}$)
t-PA = t-PA coding sequences ($thr_{263}$-$pro_{527}$)
* = serine equivalent to plasminogen $serine_{545}$/t-PA $serine_{262}$ at junction FIG. 6 Structure of pTRH34

Fragments (V)(SstI-NarI), (VI)(BanII-SstI) and linker (VIII)(NarI-BanII) are indicated.
■■ = vector sequences —— = insert DNA
◊ = restriction sites used in construction
← = other restriction sites
|——| = protein coding regions
PlgnA = plasminogen A chain coding region (glu-1 to arg-561)
t-PA B = t-PA B chain coding region (ile-276 to pro-527)

FIG. 7 Construction of pTRH00

Fragment I: is a HindIII/SfaNI fragment from the lys78-cassette plasmid.

Fragment II: is a SfaNI/BstXI fragment from pTRH34 containing most of K1P, all of K2P and K3P and the N terminal section of K4P.

Fragment III: is a BstXI/HindIII fragment from pTRH204 containing most of K4P, all of K5P, B' and the vector sequences from pTRE12.

Figure 8:
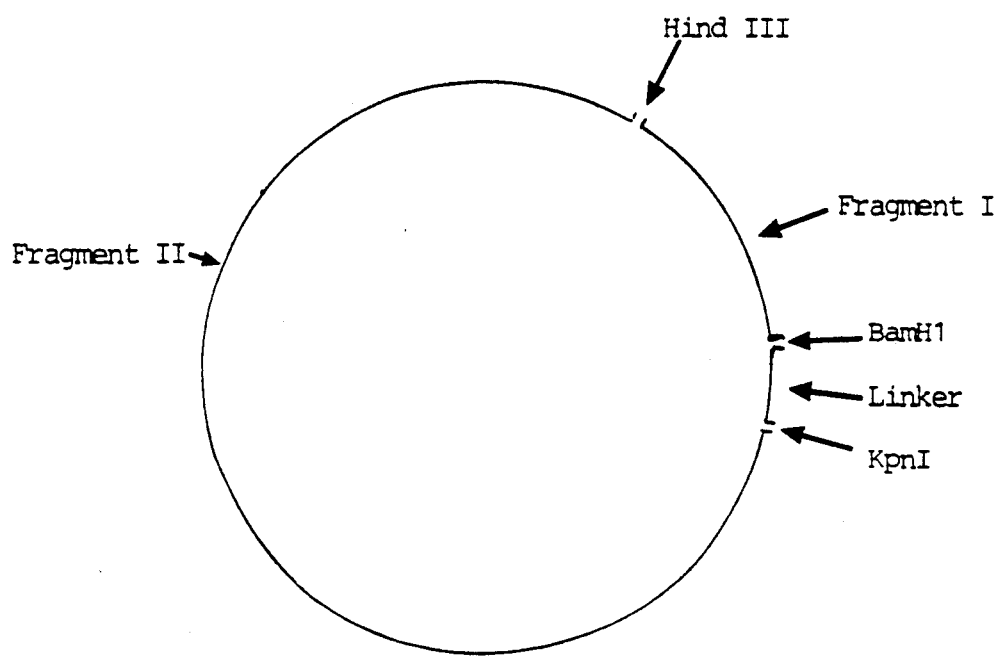

FIG. 8 Construction of pTRH01

Fragment I: is a HindIII/BamHI fragment from pTR6F encoding the t-PA finger domain and associated N-terminal and C-terminal amino acid sequences i.e. [SYQVI] F' [HSVPVKSTRATPGS], plus the 5' untranslated region and signal/pro regions.

Fragment II: is a HindIII/KpnI fragment from PTRH00 containing almost all of K1P, all of K2P, K3P, K4P, K5P, B' and the vector functions of pTRE12.

Linker: as described in Example 5.

FIG. 9 Construction of pTRH02

Fragment II: is a HindIII/BamHI fragment from pTR6FG encoding the t-PA F' and G' domains and associated linking N/C terminal sequences i.e. [SYQVI]F'[HSVPVKS]G'[EIDTRATPGS], plus the 5' untranslated region and signal/pro regions.

Fragment I: is a HindIII/KpnI fragment from PTRH00 containing almost all of K1P, all of K2P, K3P, K4P, K5P, B' and the vector functions of pTRE12.

Linker (W+X) is as described in Example 6.

FIG. 10 Structure of pTRH25

Fragment I = BglII-NarI fragment from pTRH9.
Fragment II = SstI—BglII fragment encoding urokinase B chain
III = oligonucleotides Y+Z
■ = pTRE12 sequences.
—— = insert sequences.
← = restriction sites used in construction
Plgn = plasminogen coding region (glu-1 to phe-546).
u = urokinase coding region (pro-137 to leu-411).

FIG. 11

Plasmed PSV2dhfr

P = Simian virus polyadenylation sequence  
I = Simian virus40 intron sequence  } SV40 3'

DH = dihydrofolate reductase cDNA
SV40E = Simian virus40 early promoter
EcoRI = Restriction enzyme site: EcoRI, linkered with XhoI linkers.
BglII = Restriction enzyme site: BglII.

FIG. 12 Plasmed BPV-MT-XhoI

BPV = Bovine papillomavirus sequences
MT-I = Mouse metallothionein gene sequences—including 3' polyadenylation sequence (0.3 Kb fragment B)
SstI = Restriction enzyme site: SstI, linkered with BglII linkers.
HindIII = Restriction enzyme site: HindIII, linkered with XhoI linkers.

FIG. 13 Plasmed PTRH69

MMT 3' = Mouse metallothionein polyadenylation sequences: Fragment B excised from plasmid BPV-MT-XhoI.

DH = dihydrofolate reductase cDNA  
SV40E Simian virus40 early promoter } Fragment A excised from plasmid PSV2dhfr XhoI = Restriction enzyme site XhoI
BglII = Restriction enzyme site BglII

FIG. 14 Plasmid pTRH71

LTR = Rous sarcoma virus long terminal repeat  
SV40 3' = Simian virus40 intron and polyadenylation sequences  
MUT = t-PA Mutein cDNA  } 3.3Kb fragment from pTRE24

MMT3' = Mouse metallothionein polyadenylation sequences
DH = dihydrofolate reductase cDNA
SV40E = Simian virus early promoter

FIG. 15 Plasmed pTRH11

LTR = Rous sarcoma virus long terminal repeat  
SV40 3' = Simian virus40 intron and polyadenylation sequences  
H204 = H204 hybrid protein cDNA  } 4.1Kb fragment from pTRH204

MMT3' = Mouse metallothionein polyadenylation sequences
DH = Dihydrofolate reductase cDNA
SV40E = Simian virus40 early promoter

FIGS. 16A-F

FIGS. 16A-F is the nucleotide sequence and deducted amino acid sequence of the full-length human tissue-type plasminogen activator cDNA insert depicted in FIG. 3(b) of Pennica et al, Nature, Vol. 301, Jan. 20, 1983 at page 217.

FIGS. 17A-G

FIGS. 17A-G is the cDNA sequence for plasminogen depicted in FIG. 4 of Fosgren et al, FEBS Letters, Vol. 213, No. 2, March 1987 at page 258. As stated at page 258, the bold face arrows pointing to the right and to the bottom of FIG. 17 indicate the start of the mature protein and the site of cleavage of the proenzyme, respectively. Boxed amino acids represent amino acid deviations in comparison to the published amino acid sequence. Underlining in the coding region of the DNA sequence indicates the segment used for preparation of the oligonucleotide probe. 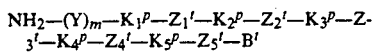 represents synthetic oligonucleotide primers. In the 3'-non-coding region, the consensus polyadenylation site is underlined.

We claim:

1. A hybrid plasminogen activator of the formula:

$$NH_2-(Y)_m-K_1{}^p-Z_1{}'-K_2{}^p-Z_2{}'-K_3{}^p-Z_3{}'-K_4{}^p-Z_4{}'-K_5{}^p-Z_5{}'-B'$$

where $B'$ comprises residues 276-527 of human t-PA, m is 0 or 1, each of $K_1{}^p$ to $K_5{}^p$ represents kringle domains 1-5, respectively, from human plasminogen, each "—" represents a bond, $Z_1{}'$, $Z_2{}'$, $Z_3{}'$ and $Z_4{}'$ represent the native human plasminogen inter-domain sequences between human plasminogen kringle domains 1 and 2, 2 and 3, 3 and 4 and 4 and 5, respectively, and Y represents a linking sequence of amino acids which may be introduced synthetically during the preparation of the hybrid plasminogen activator and/or derived from native human plasminogen and/or human t-PA sequences, the sequence $Z_5{}'$ comprising residues 262-275 of human t-PA, including one- and two-chain variants, cleavage site muteins and glycosylation site muteins of said t-PA residues.

2. A hybrid plasminogen activator according to claim 1 wherein Y represents human plasminogen residues 1 to 83 or 78 to 83 respectively.

3. A hybrid plasminogen activator according to claim 1 wherein $Z_5{}'$ is:
 1. [AAPSTCGLRQYSQPQFR],
 2. [AAPSTCGLRQYSQPQFQ], or
 3. [STCGLRQYSQPQFR].

4. Hybrid plasminogen activators selected from the group consisting of
 human plasminogen 1-544/human t-PA 262-527 including one and two chain variants, $lys_{78}$ and $glu_1$ variants, and mixtures thereof,
 human plasminogen 1-544/human t-PA 262-527 ($arg_{275} \rightarrow gln$) including one and two chain variants, $lys_{78}$ and $glu_1$ variants and mixtures thereof,
 human plasminogen 1-541/human t-PA 262-527 including one and two chain variants, $lys_{78}$ and $glu_1$ variants and mixtures thereof,
 human t-PA 1-50/human t-PA 88-91/pro-gly-ser/human plasminogen 84-544/human t-PA 262-527 including one and two chain variants, $gly_{-3}$, $ser_1$ and $val_4$ variants, and mixtures thereof, and
 human t-PA 1-91/pro-gly-ser/human plasminogen 84-544/human t-PA 262-527 including one and two chain variants, $gly_{-3}$, $ser_1$ and $val_4$ variants, and mixtures thereof.

5. Hybrid plasminogen activators selected from the group consisting of
 human plasminogen 1-544/two chain human t-PA 262-527, including $glu_1$ and $lys_{78}$ variants and mixtures thereof, wherein any catalytic site essential for fibrinolytic activity is blocked by a 2-amino-4-chlorobenzoyl removable blocking group,
 human plasminogen 1-541/two chain human t-PA 262-527, including $glu_1$ and $lys_{78}$ variants and mixtures thereof, wherein any catalytic site essential for fibrinolytic activity is blocked by a 2-amino-4-chlorobenzoyl removable blocking group, and
 human t-PA 1-91/pro-gly-ser/human plasminogen 84-544/two chain human t-PA 262-527, including $gly_{-3}$, $ser_1$ and $val_4$ variants and mixtures thereof, wherein any catalytic site essential for fibrinolytic activity is blocked by a 2-amino-4-chlorobenzoyl removable blocking group.

6. A hybrid plasminogen activator which comprises the five kringle domains of human plasminogen linked to residues 276-527 of human t-PA via an amino acid sequence comprising the residues 262-275 of human t-PA including one- and two-chain variants, cleavage site muteins and glycosylation site muteins of said t-PA residues.

7. A hybrid plasminogen activator according to claim 6, produced using Chinese hamster ovary cells containing an expression vector encoding said hybrid plasminogen activator and cultured under conditions suitable for expression of DNA encoding said hybrid plasminogen activator.

8. A hybrid plasminogen activator according to claim 6 wherein the catalytic site essential for fibrinolytic activity is blocked by a removable blocking group.

9. A hybrid plasminogen activator according to claim 8 wherein the removable blocking group is a 2-aminobenzoyl group substituted in the 3- or 4-position with a halogen atom and optionally further substituted with one or more weakly electron-withdrawing or electon-donating groups, wherein the pseudo first order rate constant for hydrolysis of the derivative is in the range $6.0 \times 10^{-5}$ to $4.0 \times 10^{-4}$ sec$^{-1}$ when measured in a buffer system consisting of 0.05M sodium phosphate, 0.1M sodium chloride, 0.01% v/v detergent comprising polyoxyethylenesorbitan monoleate having a molecular weight of approximately 1300, at pH 7.4 at 37° C.

10. A hybrid plasminogen activator according to claim 9 wherein the removable blocking group is 4-fluoro-2-aminobenzoyl, 4-chloro-2-aminobenzoyl or 4-bromo-2-aminobenzoyl.

11. A pharmaceutical composition for the treatment of thrombotic diseases, comprising an effective, non-toxic amount of a hybrid plasminogen activator according to claim 6, wherein the catalytic site essential for fibrinolytic activity is optionally blocked by a removable blocking group, in combination with a pharmaceutically acceptable carrier.

12. A pharmaceutical composition for the treatment of thrombotic diseases, which comprises an effective, non-toxic amount of a hybrid plasminogen activator of claim 9 in combination with a pharmaceutically acceptable carrier.

13. A method of treating thrombotic diseases, which comprises administering to the sufferer an effective, non-toxic amount of a hybrid plasminogen activator according to claim 6, wherein the catalytic site essential for fibrinolytic activity is optionally blocked by removable blocking groups.

14. A method of treating thrombotic diseases, which comprises administering to the sufferer an effective non-toxic amount of a hybrid plasminogen activator according to claim 9.

* * * * *